(12) United States Patent
Jansson et al.

(10) Patent No.: US 10,646,589 B2
(45) Date of Patent: *May 12, 2020

(54) THYROID STIMULATING HORMONE RECEPTOR PEPTIDES AND USES THEREOF

(71) Applicant: APITOPE INTERNATIONAL NV, Diepenbeek (BE)

(72) Inventors: Lotta Jansson, Diepenbeek (BE); Keith Martin, Chepstow Gwent (GB); David Wraith, Chepstow Gwent (GB); Andrea Jahraus, Diepenbeek (BE); Kathleen Vrolix, Diepenbeek (BE)

(73) Assignee: APITOPE INTERNATIONAL NV, Diepenbeek (BE)

( * ) Notice: Subject to any disclaimer, the term of this patent is extended or adjusted under 35 U.S.C. 154(b) by 81 days.

This patent is subject to a terminal disclaimer.

(21) Appl. No.: 15/537,577

(22) PCT Filed: Dec. 23, 2015

(86) PCT No.: PCT/IB2015/059942
§ 371 (c)(1),
(2) Date: Jun. 19, 2017

(87) PCT Pub. No.: WO2016/103213
PCT Pub. Date: Jun. 30, 2016

(65) Prior Publication Data
US 2018/0264139 A1 Sep. 20, 2018

(30) Foreign Application Priority Data

Dec. 24, 2014 (GB) .................................. 1423171.6
Nov. 16, 2015 (GB) .................................. 1520190.8
Nov. 16, 2015 (GB) .................................. 1520196.5
Nov. 16, 2015 (GB) .................................. 1520199.9

(51) Int. Cl.
| | | |
|---|---|---|
| A61K 38/04 | (2006.01) |
| C07K 5/00 | (2006.01) |
| C07K 7/00 | (2006.01) |
| C07K 16/00 | (2006.01) |
| C07K 17/00 | (2006.01) |
| A61K 48/00 | (2006.01) |
| A61K 39/00 | (2006.01) |
| C07K 14/72 | (2006.01) |
| A01K 67/027 | (2006.01) |
| A61K 38/17 | (2006.01) |
| A61P 5/14 | (2006.01) |

(52) U.S. Cl.
CPC ........ *A61K 48/0066* (2013.01); *A01K 67/027* (2013.01); *A61K 38/1796* (2013.01); *A61K 39/0005* (2013.01); *A61K 48/0083* (2013.01); *A61P 5/14* (2018.01); *C07K 14/723* (2013.01); *A01K 2207/05* (2013.01); *A01K 2227/105* (2013.01); *A01K 2267/0325* (2013.01); *A61K 2039/577* (2013.01)

(58) Field of Classification Search
None
See application file for complete search history.

(56) References Cited

U.S. PATENT DOCUMENTS 9,938,329 B2 * 4/2018 Wraith ............... A61K 39/0005
2018/0327463 A1 * 11/2018 Wraith ............... A61K 39/0005

FOREIGN PATENT DOCUMENTS

| JP | H7-506810 A | 7/1995 |
| JP | 2005-531497 A | 10/2005 |
| JP | 2016-532780 A | 10/2016 |
| KZ | 23099 A4 | 11/2010 |
| WO | WO-1993/15750 A1 | 8/1993 |
| WO | WO-200/0216410 A2 | 2/2002 |
| WO | WO-2003/018632 A2 | 3/2003 |
| WO | WO-2003/64464 A1 | 8/2003 |
| WO | WO-2007/057778 A2 | 5/2007 |
| WO | WO-2015/019302 A2 | 2/2015 |
| WO | WO-2015/022487 A1 | 2/2015 |
| WO | WO-2015019302 A2 * | 2/2015 ......... A61K 39/0005 |

OTHER PUBLICATIONS

Seach Report Issued by UK Intellectual Property Office dated Sep. 24, 2015, for Patent Application No. GB1423141.6.
Mizutori et al., Role of the transgenic human thyrotropin receptor A-subunit in thyroiditis induced by A-subunit immunization and regulatory T cell depletion, J. Translat. Immunol., 154:305-15 (2008).
Akdis et al., Role of interleukin 10 in specific immunotherapy, *J. Clin. Invest.*, 102:98-106 (1998).
Altschul et al., Gapped BLAST and PSI-BLAST: a new generation of protein database search programs, *Nucleic Acids Res.*, 25: 3389-402 (1997).
Anderton et al., Hierarchy in the ability of T cell epitopes to induce peripheral tolerance to antigens from myelin, *Eur. J. Immunol.*, 28:1251-61 (1998).
Anderton et al., Mechanisms of central and peripheral T-cell tolerance: lessons from experimental models of multiple sclerosis, *Immunol. Rev.*, 169:123-37 (1999).

(Continued)

*Primary Examiner* — Christina Bradley
*Assistant Examiner* — Zachary J Miknis
(74) *Attorney, Agent, or Firm* — Marshall, Gerstein & Borun LLP

(57) ABSTRACT

The present invention provides a composition which comprises the following Thyroid Stimulating Hormone Receptor (TSHR) peptides: (i) all or part of the amino acid sequence KKKKYVSIDVTLQQLESHKKK (SEQ ID NO: 1), or a part thereof, or a sequence having at least 60% sequence identity to SEQ ID NO:1; and (ii) all or part of the amino acid sequence GLKMFPDLTKVYSTD (SEQ ID NO: 2), or a part thereof, or a sequence having at least 60% sequence identity to SEQ ID NO:2. The present invention also relates to the use of such a composition for the prevention or suppression of activating autoantibody formation in Graves' disease.

12 Claims, 19 Drawing Sheets
Specification includes a Sequence Listing.

(56) References Cited

OTHER PUBLICATIONS

Chen et al., HLA-DRB108, DRB103/DRB30101, and DRB30202 are susceptibility genes for Graves' disease in North American Caucasians, whereas DRB107 is protective, *J. Clin. Endocrinol. Metab.*, 84:3182-6 (1999).

Chen et al., Susceptibility rather than resistance to hyperthyroidism is dominant in a thyrotropin receptor adenovirus-induced animal model of Graves' disease as revealed by BALB/c-C57BL/6 hybrid mice, *Endocrinol.*, 145 (11): 4927-33 (2004).

Creighton Proteins Structures and Molecular Principles, WH Freeman and Co, New York, NY(1983).

Fugger et al., Expression of HLA-DR4 and human CD4 transgenes in mice determines the variable region beta-chain T-cell repertoire and mediates an HLA-DR-restricted immune response, *Proc. Natl. Acad. Sci.*, 91:6151-55 (1994).

Holm et al., Touring protein fold space with Dali/FSSP, *Nucleic Acid Res.*, 26:316-9 (1998).

Holm, Dali: a network tool for protein structure comparison, *Trends Biochem. Sci.*, 20:478-80 (1995).

Holm, Protein structure comparison by alignment of distance matrices, *J. Mol. Biol.*, 233:123-38 (1993).

Inaba et al., Immune Response of Mice Transgenic for Human Histocompatibility Leukocyte Antigen-DR to Human Thyrotropin Receptor-Extracellular Domain, *Thyroid*, 19(11):1271-80 (2009).

International Preliminary Report on Patentability, European Patent Office, PCT/IB2015/059942, dated Jun. 27, 2017.

International Search Report and Written Opinion of the International Search Authority, European Patent Office, PCT/IB2015/059942, dated May 27, 2016.

Jeong et al., Prolyl carboxypeptidase regulates energy expenditure and the thyroid axis, *Endocrinology*, 153:683-9 (2012).

Liu et al., Affinity for class II MHC determines the extent to which soluble peptides tolerize autoreactive T cells in naive and primed adult mice—implications for autoimmunity, *Int. Immunol.*, 7:1255 (1995).

McLachlan et al., Long term persistence of thyrotropin receptor antibodies in wild-type and transgenic mice in a Graves' disease model, *Thyroid*, 8:1-7 (2012).

Metzler et al., Inhibition of experimental autoimmune encephalomyelitis by inhalation but not oral administration of the encephalitogenic peptide: influence of MHC binding affinity, *Int. Immunol.*, 5:1159-65 (1993).

Mikos Bodansky, Peptide Chemistry, A practical Textbook. Springer-Verlag, Berlin.

Mozes et al., Spontaneous autoimmune disease in (NZB × NZW)F1 mice is ameliorated by treatment with methimazole, *J. Clin Immunol.*, 18(2):106-13 (1998).

Muehlberg et al., Dynamics of thyroid-stimulating and blocking antibodies to the thyrotropin receptor in a murine model of graves' disease, Endocrinol., 145(4):1539-45 (2004).

Muller et al., Successful immunotherapy with T-cell epitope peptides of bee venom phospholipase A2 induces specific T-cell anergy in patients allergic to bee venom, *J. Allergy Clin Immunol.*, 101:747-54 (1998).

Myers et al., Align Cabios, 4: 1-17(1988).

Pearson et al., Improved tools for biological sequence comparison, *Proc. Natl. Acad. Sci.*, 85:2444-8 (1988).

Pearson, Rapid and sensitive sequence comparison with FASTP and FASTA, *Methods Enzymol.*, 183: 63-98 (1990).

Roberge et al., A strategy for a convergent synthesis of N-linked glycopeptides on a solid support, *Science*, 269:202-4 (1995).

Sanders et al., Crystal structure of the TSH receptor bound to a blocking type TSHR autoantibody, *J. Molec. Endocrinol.*, (2011).

Thompson et al., CLUSTAL W: improving the sensitivity of progressive multiple sequence alignment through sequence weighting, position-specific gap penalties and weight matrix choice, *Nucleic Acids Res.*, 22: 4673-80 (1994).

Wang et al, Methimazole protects from experimental autoimmune uveitis (EAU) by inhibiting antigen presenting cell function and reducing antigen priming, *J. Leukoc. Biol.*, 73:57-64 (2003).

McLachlan et al., Role of self-tolerance and chronic stimulation in the long-term persistence of adenovirus-induced thyrotropin receptor antibodies in wild-type and transgenic mice, *Thyroid.* 22:931-7 (2012).

Search report with translation from Russian Application No. 2017126212/10, dated Jun. 18, 2019.

Official Action, Russian Patent Application 2017126212, dated Oct. 9, 2019 (Russian with English Translation).

Tokuriki et al., Stability effects of mutations and protein evolvability, *Curr. Opin. Struct. Biol.* 19:596-604 (2009).

Inaba et al., The Role of Glutamic or Aspartic Acid in Position Four of the Epitope Binding Motif and Thyrotropin Receptor-Extracellular Domain Epitope Selection in Graves' Disease, *J Clin Endocrinol Metab.* 95:2909-16 (2010).

Kellermann et al., TSH Receptor Sequences Recognized by CD4+T Cells in Graves' Disease Patients and Healthy Controls, *Journal of Autoimmunity.* 8:685-98 (abstract) (1995).

Martin et al., Detection of major T-cell epitopes on human TSH receptor by overriding immune heterogeneity in patients with Graves' disease, *J Clin Endocrinol Metal.* 82:3361-6 (1997).

Tandon et al., T cell responses to synthetic TSH receptor peptides in Graves' disease, *Clin Exp Immunol.* 89:468-73 (1992).

Wu et al., Induction of Murine Neonatal Tolerance Against Graves' Disease Using Recombinant Adenovirus Expressing the TSH Receptor A-Subunit, *Endocrinology.* 152:1165-71 (2011).

Notice of Reasons for Refusal dated Aug. 14, 2019, Japanese Patent Application No. 2017-534205 (Japanese with English translation).

\* cited by examiner

A

B

C

D

A

B

A

B

C

D

A

B

SEQUENCE LISTING

```
<160> NUMBER OF SEQ ID NOS: 4

<210> SEQ ID NO 1
<211> LENGTH: 21
<212> TYPE: PRT
<213> ORGANISM: Artificial Sequence
<220> FEATURE:
<223> OTHER INFORMATION: Thyroid Stimulating Hormone Receptor (TSHR)
      peptide RNB-5D-K1

<400> SEQUENCE: 1

Lys Lys Lys Lys Tyr Val Ser Ile Asp Val Thr Leu Gln Gln Leu Glu
1               5                   10                  15

Ser His Lys Lys Lys
            20

<210> SEQ ID NO 2
<211> LENGTH: 15
<212> TYPE: PRT
<213> ORGANISM: Artificial Sequence
<220> FEATURE:
<223> OTHER INFORMATION: TSHR peptide RNB-9B

<400> SEQUENCE: 2

Gly Leu Lys Met Phe Pro Asp Leu Thr Lys Val Tyr Ser Thr Asp
1               5                   10                  15

<210> SEQ ID NO 3
<211> LENGTH: 764
<212> TYPE: PRT
<213> ORGANISM: Homo sapiens

<400> SEQUENCE: 3

Met Arg Pro Ala Asp Leu Leu Gln Leu Val Leu Leu Leu Asp Leu Pro
1               5                   10                  15

Arg Asp Leu Gly Gly Met Gly Cys Ser Ser Pro Pro Cys Glu Cys His
            20                  25                  30

Gln Glu Glu Asp Phe Arg Val Thr Cys Lys Asp Ile Gln Arg Ile Pro
        35                  40                  45

Ser Leu Pro Pro Ser Thr Gln Thr Leu Lys Leu Ile Glu Thr His Leu
    50                  55                  60

Arg Thr Ile Pro Ser His Ala Phe Ser Asn Leu Pro Asn Ile Ser Arg
65                  70                  75                  80

Ile Tyr Val Ser Ile Asp Val Thr Leu Gln Gln Leu Glu Ser His Ser
                85                  90                  95

Phe Tyr Asn Leu Ser Lys Val Thr His Ile Glu Ile Arg Asn Thr Arg
            100                 105                 110
```

```
Asn Leu Thr Tyr Ile Asp Pro Asp Ala Leu Lys Glu Leu Pro Leu Leu
            115                 120                 125

Lys Phe Leu Gly Ile Phe Asn Thr Gly Leu Lys Met Phe Pro Asp Leu
        130                 135                 140

Thr Lys Val Tyr Ser Thr Asp Ile Phe Phe Ile Leu Glu Ile Thr Asp
145                 150                 155                 160

Asn Pro Tyr Met Thr Ser Ile Pro Val Asn Ala Phe Gln Gly Leu Cys
                165                 170                 175

Asn Glu Thr Leu Thr Leu Lys Leu Tyr Asn Asn Gly Phe Thr Ser Val
            180                 185                 190

Gln Gly Tyr Ala Phe Asn Gly Thr Lys Leu Asp Ala Val Tyr Leu Asn
        195                 200                 205

Lys Asn Lys Tyr Leu Thr Val Ile Asp Lys Asp Ala Phe Gly Gly Val
210                 215                 220

Tyr Ser Gly Pro Ser Leu Leu Asp Val Ser Gln Thr Ser Val Thr Ala
225                 230                 235                 240

Leu Pro Ser Lys Gly Leu Glu His Leu Lys Glu Leu Ile Ala Arg Asn
                245                 250                 255

Thr Trp Thr Leu Lys Lys Leu Pro Leu Ser Leu Ser Phe Leu His Leu
            260                 265                 270

Thr Arg Ala Asp Leu Ser Tyr Pro Ser His Cys Cys Ala Phe Lys Asn
        275                 280                 285

Gln Lys Lys Ile Arg Gly Ile Leu Glu Ser Leu Met Cys Asn Glu Ser
290                 295                 300

Ser Met Gln Ser Leu Arg Gln Arg Lys Ser Val Asn Ala Leu Asn Ser
305                 310                 315                 320

Pro Leu His Gln Glu Tyr Glu Glu Asn Leu Gly Asp Ser Ile Val Gly
                325                 330                 335

Tyr Lys Glu Lys Ser Lys Phe Gln Asp Thr His Asn Asn Ala His Tyr
            340                 345                 350

Tyr Val Phe Phe Glu Glu Gln Glu Asp Glu Ile Ile Gly Phe Gly Gln
        355                 360                 365

Glu Leu Lys Asn Pro Gln Glu Glu Thr Leu Gln Ala Phe Asp Ser His
370                 375                 380

Tyr Asp Tyr Thr Ile Cys Gly Asp Ser Glu Asp Met Val Cys Thr Pro
385                 390                 395                 400

Lys Ser Asp Glu Phe Asn Pro Cys Glu Asp Ile Met Gly Tyr Lys Phe
                405                 410                 415

Leu Arg Ile Val Val Trp Phe Val Ser Leu Leu Ala Leu Leu Gly Asn
            420                 425                 430

Val Phe Val Leu Leu Ile Leu Leu Thr Ser His Tyr Lys Leu Asn Val
        435                 440                 445

Pro Arg Phe Leu Met Cys Asn Leu Ala Phe Ala Asp Phe Cys Met Gly
450                 455                 460

Met Tyr Leu Leu Leu Ile Ala Ser Val Asp Leu Tyr Thr His Ser Glu
465                 470                 475                 480

Tyr Tyr Asn His Ala Ile Asp Trp Gln Thr Gly Pro Gly Cys Asn Thr
                485                 490                 495

Ala Gly Phe Phe Thr Val Phe Ala Ser Glu Leu Ser Val Tyr Thr Leu
            500                 505                 510

Thr Val Ile Thr Leu Glu Arg Trp Tyr Ala Ile Thr Phe Ala Met Arg
        515                 520                 525
```

```
Leu Asp Arg Lys Ile Arg Leu Arg His Ala Cys Ala Ile Met Val Gly
    530                 535                 540
Gly Trp Val Cys Cys Phe Leu Leu Ala Leu Leu Pro Leu Val Gly Ile
545                 550                 555                 560
Ser Ser Tyr Ala Lys Val Ser Ile Cys Leu Pro Met Asp Thr Glu Thr
                565                 570                 575
Pro Leu Ala Leu Ala Tyr Ile Val Phe Val Leu Thr Leu Asn Ile Val
            580                 585                 590
Ala Phe Val Ile Val Cys Cys Tyr Val Lys Ile Tyr Ile Thr Val
        595                 600                 605
Arg Asn Pro Gln Tyr Asn Pro Gly Asp Lys Asp Thr Lys Ile Ala Lys
    610                 615                 620
Arg Met Ala Val Leu Ile Phe Thr Asp Phe Ile Cys Met Ala Pro Ile
625                 630                 635                 640
Ser Phe Tyr Ala Leu Ser Ala Ile Leu Asn Lys Pro Leu Ile Thr Val
                645                 650                 655
Ser Asn Ser Lys Ile Leu Leu Val Leu Phe Tyr Pro Leu Asn Ser Cys
            660                 665                 670
Ala Asn Pro Phe Leu Tyr Ala Ile Phe Thr Lys Ala Phe Gln Arg Asp
    675                 680                 685
Val Phe Ile Leu Leu Ser Lys Phe Gly Ile Cys Lys Arg Gln Ala Gln
    690                 695                 700
Ala Tyr Arg Gly Gln Arg Val Pro Pro Lys Asn Ser Thr Asp Ile Gln
705                 710                 715                 720
Val Gln Lys Val Thr His Asp Met Arg Gln Gly Leu His Asn Met Glu
                725                 730                 735
Asp Val Tyr Glu Leu Ile Glu Asn Ser His Leu Thr Pro Lys Lys Gln
            740                 745                 750
Gly Gln Ile Ser Glu Glu Tyr Met Gln Thr Val Leu
        755                 760

<210> SEQ ID NO 4
<211> LENGTH: 21
<212> TYPE: PRT
<213> ORGANISM: Artificial Sequence
<220> FEATURE:
<223> OTHER INFORMATION: TSHR peptide RNB-4K-GKK

<400> SEQUENCE: 4

Lys Lys Gly Asn Leu Pro Asn Ile Ser Arg Ile Tyr Val Ser Ile Asp
1               5                   10                  15

Val Thr Gly Lys Lys
            20
```

THYROID STIMULATING HORMONE RECEPTOR PEPTIDES AND USES THEREOF

CROSS-REFERENCE TO RELATED APPLICATIONS

This application is a U.S. National Phase application of International Patent Application No. PCT/IB2015/059942 filed Dec. 23, 2015, which claims priority benefit of United Kingdom Application Nos. 1520190.8 filed Nov. 16, 2015; 1520196.5 filed Nov. 16, 2015; 1520199.9 filed Nov. 16, 2015; and 1423171.6 filed Dec. 24, 2014.

INCORPORATION BY REFERENCE OF MATERIALS SUBMITTED ELECTRONICALLY

This application contains, as a separate part of the disclosure, a Sequence Listing in computer readable form (Filename: 52090_Seqlisting.txt; Size: 7,831 bytes; Created: Jun. 16, 2017), which is incorporated by reference in its entirety.

FIELD OF THE INVENTION

The present invention relates to a composition which comprises peptides derived from Thyroid Stimulating Hormone Receptor (TSHR). The composition or peptides may be useful in the prevention and/or suppression of production of TSHR autoantibodies, which is useful in the treatment and/or prevention of Graves' disease.

BACKGROUND TO THE INVENTION

Graves' disease is an autoimmune disease that affects the thyroid. It is characterised by an overactive thyroid gland, which results in the production of an excessive amount of thyroid hormone and enlargement of the thyroid gland (goitre). The resulting state of hyperthyroidism may cause a wide range of neuropsychological and physical symptoms. Graves' disease is the most common cause of hyperthyroidism (60-90% of all cases) and usually presents itself during midlife, but also appears in children, adolescents, and the elderly. It affects up to 2% of the female population and is between five and ten times as common in females as in males. Paediatric Graves' disease affects about 6,000 children in the United States (US) and 6,000 in the European Union (EU). Graves' disease is also the most common cause of severe hyperthyroidism, which is accompanied by more clinical signs and symptoms and laboratory abnormalities as compared with milder forms of hyperthyroidism.

There is a strong hereditary component linked to Graves' disease. There are no recent population studies on Graves' disease, however, a few quasi population studies on hyperthyroidism do exist and all estimates for incidence and prevalence of Graves' disease are thus approximate. The incidence of hyperthyroidism varies from 26:100,000 to 93:100,000 and the overall prevalence is estimated to be at 1.3%, with 40% of cases being overt and 60% subclinical.

About 30-50% of people with Graves' disease will also suffer from Graves' opthalmopathy (also known as Graves' orbitopathy or thyroid eye disease) (GO), a protrusion of one or both eyes. Many cases of GO are mild and self-limiting, however 20% of cases have significant/moderate to severe disease, with at least half of these requiring steroids and 3-5% of GO patients have painful, sight-threatening disease with dysthyroid optic neuropathy. The buldging of the eyes may cause severe dryness of the cornea as the eye lids are unable to close at night. Increased pressure on the optic nerve can lead to visual field defects and vision loss. GO may also be associated with pretibial myxedemia.

The symptoms and signs of Graves' disease virtually all result from the direct and indirect effects of hyperthyroidism, with main exceptions being GO, goitre and pretibial myxedema. Symptoms of hyperthyroidism may include insomnia, hand tremor, hyperactivity, hair loss, excessive sweating, heat intolerance and weight loss despite increased appetite. Further signs are most commonly a diffusely enlarged (usually symmetric) non-tender thyroid, lid lag, excessive lacrimation due to GO, arrhythmias of the heart and hypertension. Thyrotoxic patients may experience behavioural and personality changes, such as psychosis, agitation, and depression. In milder hyperthyroidism, patients may experience less overt manifestations, for example anxiety, restlessness, irritability and emotional lability.

There is currently no cure available for Graves' disease and present treatments are therefore directed towards targeting the presenting symptoms. There are three treatment modalities for Graves' disease, oral antithyroid drugs (ATDs), radioactive iodine (RAI) and thyroidectomy. The latter two approaches result in lifetime supplementation of thyroid hormones. Therapy with RAI is the most common treatment in the US, whilst ATDs are the first line treatment in Europe, Japan and most of the rest of the world.

ATD therapy is associated with some rare side-effects and has a remission rate of 50-60%. There is growing recognition that RAI can precipitate or worsen active GO and the number of patients treated with ATDs is the United States is increasing.

Due to the varying success of each treatment option, patients are often subjected to more than one approach if the first attempted treatment does not prove entirely successful. The risk of relapse or subsequent hypothyroidism is substantial and the general efficacy of available treatments for Graves' disease is less than desired.

The development of alternative therapies for Graves' disease has been hampered by a lack of relevant models, in particular animal models, for assessing the potential efficacy of candidate therapies. Known BALB/c mouse models for Graves' disease have not been tested for efficacy with approved drugs for Graves' disease, such as methimazole and methylprednisolone.

There is thus a need for alternative therapies for treating and preventing diseases associated with the production of TSHR autoantibodies, such as Graves' disease. Alternative therapies that are effective at treating Graves' disease and at alleviating or reducing the symptoms of the disease are thus needed. There is also a need for alternative models for assessing the potential efficacy of candidate Graves' disease therapies.

SUMMARY OF ASPECTS OF THE INVENTION

The present inventors have found that a "cocktail" of two TSHR peptides is particularly effective in suppressing or preventing the production of TSHR autoantibodies in vivo and in treating Graves' disease.

Thus in a first aspect the present invention provides a composition which comprises the following TSHR peptides:

(i) all or part of the amino acid sequence KKKKYVSIDVTLQQLESHKKK (SEQ ID NO: 1), or a part thereof, or a sequence having at least 60% sequence identity to SEQ ID NO:1; and (ii) all or part of the amino acid sequence GLKMFPDLTKVYSTD (SEQ ID NO: 2), or a part thereof, or a sequence having at least 60% sequence identity to SEQ ID NO:2.

KKKKYVSIDVTLQQLESHKKK (SEQ ID NO: 1) is also referred to as RNB-5D-K1 herein. GLKMFPDLTK-VYSTD (SEQ ID NO: 2) is also referred to as RNB-9B herein.

The composition according to the invention may be used in the therapeutic aspects of the invention described herein.

In a second aspect the present invention provides a peptide of the invention as described herein, for use in suppressing or preventing the production of TSHR autoantibodies in vivo.

In a third aspect the present invention provides a peptide of the invention as described herein for use in treating and/or preventing Graves' disease in a subject.

In a fourth aspect the present invention provides the use of a peptide of the invention as described herein, in the manufacture of a medicament to suppress or prevent the production of TSHR autoantibodies in vivo.

In a fifth aspect the present invention relates to the use of a peptide of the invention as described herein, in the manufacture of a medicament to treat and/or prevent Graves' disease.

In a sixth aspect the present invention relates to a method for suppressing or preventing the production of TSHR autoantibodies in a subject, which comprises the step of administration of all or a part of a peptide of SEQ ID NO:1 or a peptide with at least 60% sequence identity thereto, and all or a part of a peptide of SEQ ID NO:2 or a peptide with at least 60% sequence identity thereto, to the subject.

In a seventh aspect the present invention relates to a method for treating Graves' disease in a subject which comprises the step of administration of all or a part of a peptide of SEQ ID NO:1 or a peptide with at least 60% sequence identity thereto and all or a part of a peptide of SEQ ID NO:2 or a peptide with at least 60% sequence identity thereto to the subject.

In one aspect, the composition does not include or comprise the following peptide:

```
RNB-4K-GKK: KKGNLPNISRIYVSIDVTGKK  (SEQ ID NO: 4)
```

A peptide composition according to the invention may comprise the amino acid sequences according to the invention as described herein. In one aspect the peptide composition comprises only the amino acid sequences according to the invention as described herein.

The subject may be HLA-DR3. The subject may be HLA-DR4.

The peptides of the invention as defined herein, or the composition of the invention, may be administered following a dose-escalation protocol.

In an eighth aspect the present invention relates to a kit which comprises the following TSHR peptides:

(i) all or part of the amino acid sequence KKKKYVSIDVTLQQLESHKKK (SEQ ID NO: 1), or a part thereof, or a sequence having at least 60% sequence identity to SEQ ID NO:1;
and
(ii) all or part of the amino acid sequence GLKMFPDLTKVYSTD (SEQ ID NO: 2), or a part thereof, or a sequence having at least 60% sequence identity to SEQ ID NO:2;

for simultaneous, separate or sequential administration.

The kit may be for the treatment or prevention of a condition involving the production of TSHR autoantibodies, such as Graves' Disease.

In a ninth aspect of the invention the peptides or composition of the invention is combined with a further therapeutic agent that is used in the treatment, prevention or management of Graves' Disease. For example, the peptides or composition may be combined with an antithyroid drug, or a β-blocker.

In a ninth aspect the present invention relates to an animal model for a disease associated with the production of TSHR antibodies, wherein the animal is transgenic for human HLA-DR3 and wherein levels of TSHR are increased in the animal relative to a suitable control animal. In one aspect the level of TSHR is increased by administration of a viral vector comprising a nucleic acid molecule encoding a TSHR peptide.

The disease associated with the production of TSHR antibodies may be Graves' Disease.

The TSHR may be human TSHR. For example the TSHR may be human TSHR A subunit or extracellular domain (ECD).

The viral vector may be an adenoviral vector or adenoviral construct.

The adenoviral vector or construct may be administered at three-week intervals. The adenoviral vector or construct may be administered in two or three sequential administrations.

The adenoviral vector or construct is administered at a dose of $10^9$ to $10^{11}$ viral particles. The adenoviral vector or construct may be administered by intramuscular injection.

The animal may be a mouse. The mouse may be a HLA-BRD1*0301 transgenic mouse.

DESCRIPTION OF THE FIGURES

FIG. 1—5D-K1 treatment reduces TSHR-induced proliferation in DR3tg mice

DR3tg mice were pretreated with 5D-K1 (GLS) or control (HLA-DR3 binding peptide; GLS) (n=10/group) according to the dose escalation schedule with 100 μg top dose. Animals received an immunization of 50 μg 5D (GLS) in CFA and after 10 days, LN and spleens were harvested to assess the TSHR-specific proliferation. Data represent mean±standard error of the mean (SEM) of stimulation index (SI) values for the control-treated mice (red lines) and peptide-treated mice (blue lines). Two-way ANOVA was used to measure overall treatment effects on T cell proliferation and p-values are written in the graphs. Bonferonni post-hoc testing was used and significant differences are indicated in the graphs (*$p<0.05$; $p<0.01$; *$p<0.001$: ****$p<0.0001$). The average percentage reduction in T cell proliferation induced by peptide-treatment is shown in the graph. SI, stimulation index; LN; lymph nodes.

FIGS. 2-9B-N treatment reduces TSHR-induced proliferation in DR3tg mice.

DR3tg mice were pretreated with 9B-N (PPL) or PBS (n=10/group) according to the dose escalation schedule with 33 μg top dose. Animals received an immunization of 50 μg 9B (GLS) in CFA and after 10 days, LN and spleens were harvested to assess the TSHR-specific proliferation. Data represent mean±standard error of the mean (SEM) of stimulation index (SI) values for the control-treated mice (red lines) and peptide-treated mice (blue lines). Two-way ANOVA was used to measure overall treatment effects on T cell proliferation and p-values are written in the graphs. Bonferonni post-hoc testing was used and significant differences are indicated in the graphs (*$p<0.05$; $p<0.01$; *$p<0.001$: ****$p<0.0001$). The average percentage reduction in T cell proliferation induced by peptide-treatment is shown in the graph. SI, stimulation index; LN; lymph nodes.

Figure 3:
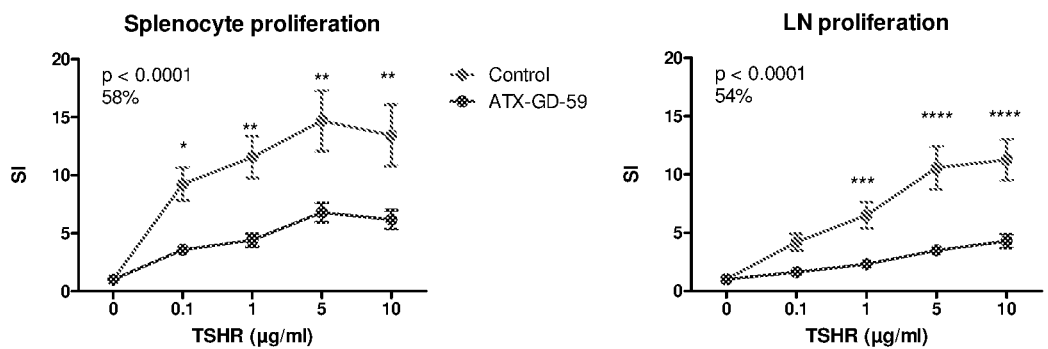

FIG. 3—ATX-GD-59 treatment reduces TSHR-induced proliferation in DR3tg mice

DR3tg mice were pretreated with ATX-GD-59 (PPL) or HIP-15F-GKK control peptide (GLS) (n=10/group) according to the dose escalation schedule with 15 nmol top dose for each peptide. Animals received an immunization of 30 nmol of each parental peptide 5D (Severn) and 9B (PPL) in CFA and after 10 days, LN and spleens were harvested to assess the TSHR-specific proliferation. Data represent mean±standard error of the mean (SEM) of stimulation index (SI) values for the control-treated mice (red lines) and peptide-treated mice (blue lines). Two-way ANOVA was used to measure overall treatment effects on T cell proliferation and p-values are written in the graphs. Bonferonni post-hoc testing was used and significant differences are indicated in the graphs (*p<0.05; p<0.01; *p<0.001; ****p<0.0001). The average percentage reduction in T cell proliferation induced by peptide-treatment is shown in the graph. SI, stimulation index; LN; lymph nodes. Data are representative for 2 independent experiments.

Figure 4:
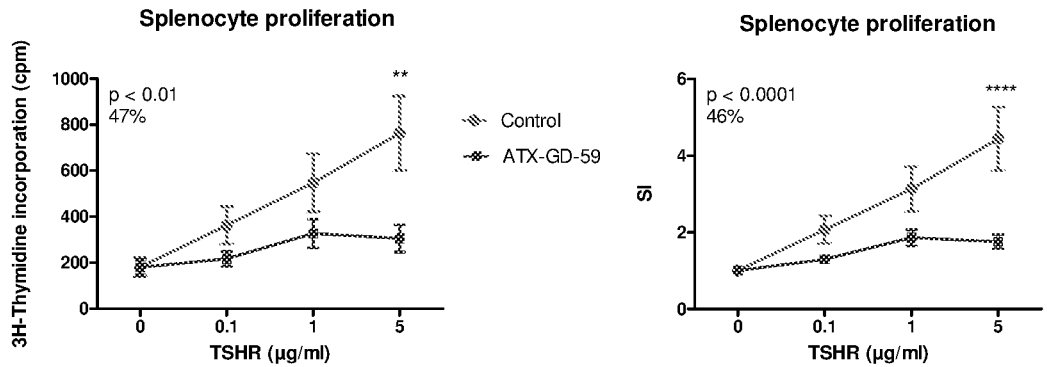

FIG. 4—ATX-GD-59 treatment reduces TSHR-specific splenocyte proliferation in Ad-TSHR immunized DR3tg mice DR3tg mice (n=11/group) were injected subcutaneously in the flank region with 22.5 pmol, 225 pmol and 2250 pmol ATX-GD-59 or control treatment on days −15, −13 and −11, followed by 3 injections of 22.5 nmol/peptide of ATX-GD-59 or control treatment on days −8, −6 and −4 (dose escalation schedule). Then, mice were injected intramuscularly with 1010 Ad-TSHR or Ad-LacZ on two occasions on a three weekly interval (day 0 and 21). The experiment was terminated 5 weeks after the first immunization and spleens were harvested to assess the TSHR-specific proliferation. Data represent mean±standard error of the mean (SEM) of absolute counts per minute (cpm; left graph) or stimulation index (SI; right graph) values for the control-treated mice (red lines) and peptide-treated mice (blue lines). Two-way ANOVA was used to measure overall treatment effects on T cell proliferation and p-values are written in the graphs. Bonferonni post-hoc testing was used and significant differences are indicated in the graphs (*p<0.05; p<0.01; *p<0.001; ****p<0.0001). The overall average percentage reduction in T cell proliferation induced by peptide-treatment is shown in the graph. Data are representative for 2 independent experiments.

Figure 5:
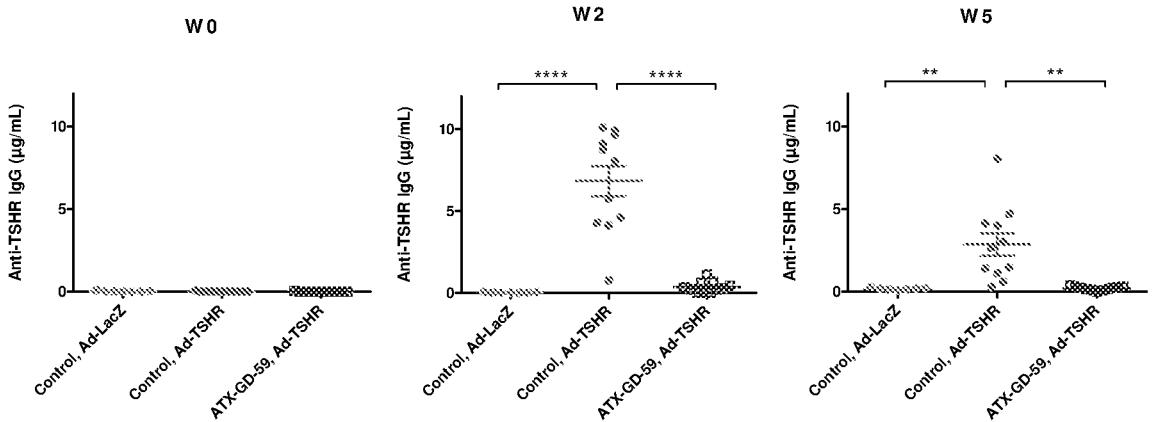

FIG. 5—Prophylactic ATX-GD-59 treatment reduces anti-TSHR antibody level

DR3tg mice were injected subcutaneously in the flank region with 22.5 pmol, 225 pmol and 2250 pmol ATX-GD-59 (n=11) or control treatment (n=11) on days −15, −13 and −11, followed by 3 injections of 22.5 nmol of each peptide in ATX-GD-59 or control treatment on days −8, −6 and −4 (dose escalation schedule). Then, mice were injected intramuscularly with 1010 Ad-TSHR or Ad-LacZ (n=7) on two occasions on a three weekly interval (day 0 and 21). Blood was collected before treatment and before and 2 and 5 weeks after the first immunization to measure anti-TSHR total IgG levels by ELISA. Each dot represent data from one mouse and group average±SEM are indicated. One-way ANOVA was used to measure overall differences in anti-TSHR IgG levels. Bonferroni post-hoc testing was used and significant differences are indicated in the graphs (*p<0.05; p<0.01; *p<0.001; ****p<0.0001). Data are representative for 2 independent experiments.

Figure 6:
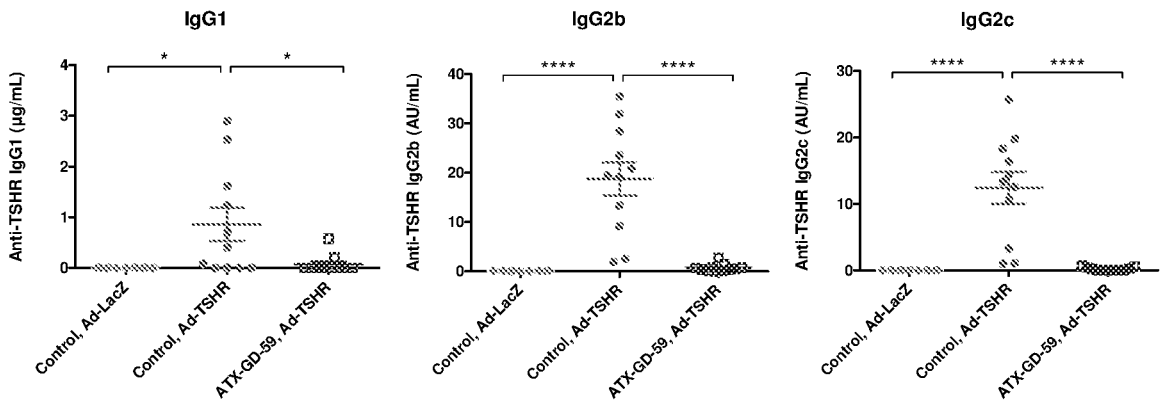

FIG. 6—Prophylactic ATX-GD-59 treatment reduces different anti-TSHR antibody isotype levels DR3tg mice were injected subcutaneously in the flank region with 22.5 pmol, 225 pmol and 2250 pmol ATX-GD-59 (n=11) or control treatment (n=11) on days −15, −13 and −11, followed by 3 injections of 22.5 nmol of each peptide in ATX-GD-59 or control treatment on days −8, −6 and −4 (dose escalation schedule). Then, mice were injected intramuscularly with $10^{10}$ Ad-TSHR or Ad-LacZ (n=7) on two occasions on a three weekly interval (day 0 and 3). Blood was collected before treatment and before and 2 and 5 weeks after the first immunization; anti-TSHR isotype IgG levels were measured at week 2 by ELISA. Each dot represent data from one mouse and group average±SEM are indicated. One-way ANOVA was used to measure overall differences in anti-TSHR IgG levels. Bonferroni post-hoc testing was used and significant differences are indicated in the graphs (*p<0.05; p<0.01; *p<0.001; ****p<0.0001). Data are representative for 2 independent experiments.

Figure 7:
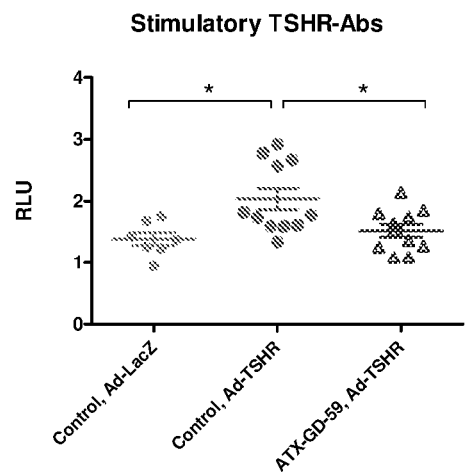

FIG. 7—Incidence of stimulatory anti-TSHR antibodies in Ad-TSHR immunized DR3tg mice DR3tg mice were injected subcutaneously in the flank region with 22.5 pmol, 225 pmol and 2250 pmol ATX-GD-59 (n=11) or control treatment (n=11) on days −15, −13 and −11, followed by 3 injections of 22.5 nmol of each peptide in ATX-GD-59 or control treatment on days −8, −6 and −4 (dose escalation schedule). Then, mice were injected intramuscularly with 1010 Ad-TSHR or Ad-LacZ (n=7) on two occasions on a three weekly interval (day 0 and 3). Serum was collected 5 weeks after the first immunization and analysed in the CHO-cell assay. Each dot represents data from one mouse at week 5 and average±SEM are shown per group. Mann-Whitney test was used to measure differences in stimulatory TSHR-antibody levels and significant differences are indicated in the graphs (*p<0.05; p<0.01; *p<0.001; ****p<0.0001). Results are representative for more than 3 independent experiments. RLU, relative light units (light emission of stimulated cells/light emission of non-stimulated cells).

Figure 8:
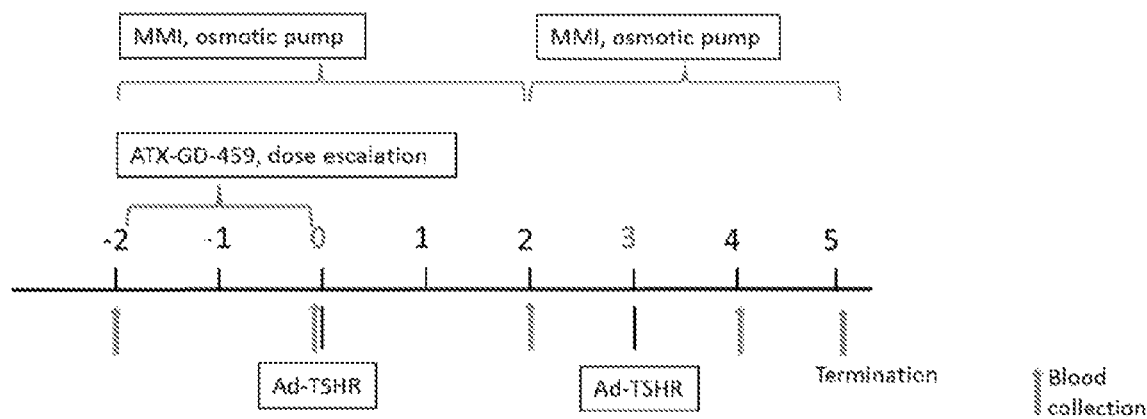

FIG. 8—Schematic overview of MMI and ATX-GD-459 co-medication study

Mice were injected subcutaneously in the flank region with 15 pmol, 150 pmol and 1500 pmol of each ATX-GD-459 peptide or control peptide on days −15, −13 and −11, followed by 3 injections of 15 nmol of each ATX-GD-459 peptide or control peptide on days −8, −6 and −4 (dose escalation schedule). Starting on day −15, mice also received vehicle or methimazole treatment via a subcutaneously implanted osmotic pump. Then, mice were injected intramuscularly with 109 Ad-TSHR particles on two occasions at a three weekly interval (week 0 and 3). Blood was collected at 2 weeks and immediately before treatment and then 2, 4 and 5 weeks after the first immunization. The experiment was terminated 5 weeks after the first immunization to obtain blood, thyroid and spleen samples.

Figure 9:
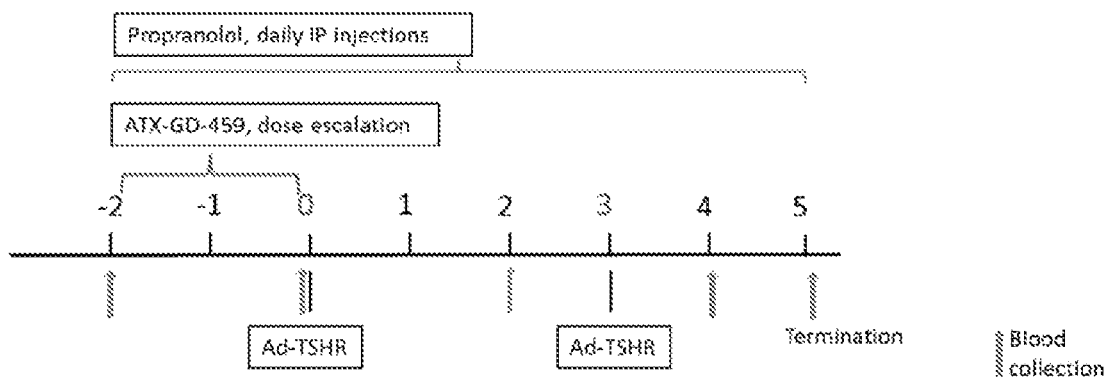

FIG. 9—Schematic overview of propranolol and ATX-GD-459 co-medication study

Mice were injected subcutaneously in the flank region with 15 pmol, 150 pmol and 1500 pmol of each ATX-GD-459 peptide or control peptide on days −15, −13 and −11, followed by 3 injections of 15 nmol of each ATX-GD-459 peptide or control peptide on days −8, −6 and −4 (dose escalation schedule). Starting on day −15, mice also received vehicle or propranolol treatment via daily intraperitoneal injections. Then, mice were injected intramuscularly with 1010 Ad-TSHR particles on two occasions on a three weekly interval (week 0 and 3). Blood was collected 2 weeks and immediately before treatment and then 2, 4 and 5 weeks after the first immunization. The experiment was terminated 5 weeks after the first immunization to obtain blood, thyroid and spleen samples.

Figure 10:
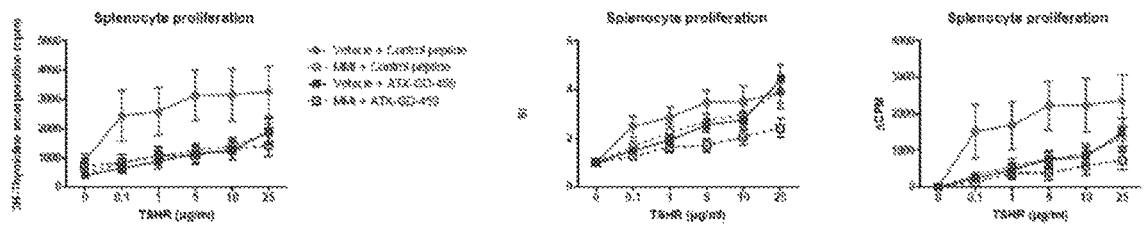

FIG. 10—TSHR-specific splenocyte proliferation in Ad-TSHR immunized DR3tg mice

DR3tg mice (n=7-10/group) were injected subcutaneously in the flank region with 15 pmol, 150 pmol and 1500 pmol ATXGD-459 or control treatment on days −15, −13 and −11, followed by 3 injections of 15 nmol ATX-GD-459 or control treatment on days −8, −6 and −4 (dose escalation schedule). Starting on day −15, mice also received vehicle (full symbols) or MMI (open symbols) treatment via a subcutaneously implanted osmotic pumps. Then, mice were injected intramuscularly with 109 Ad-TSHR on two occasions on a three weekly interval (day 0 and 3). The experiment was terminated 5 weeks after the first immunization and spleens were harvested to assess the TSHR-specific proliferation Data represent mean±standard error of the mean (SEM) of absolute counts per minute (cpm; left graph), stimulation index values (SI; middle graph) or corrected counts (Δcpm; right graph). Two-way ANOVA was used to measure overall treatment effects on T cell proliferation and Bonferonni post-hoc testing was used. Significant differences are described in the text.

Figure 11:
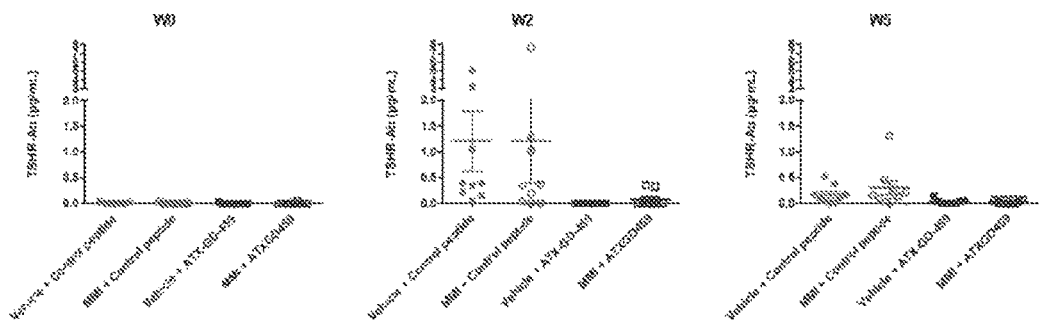

FIG. 11—ATX-GD-459 but not MMI treatment reduces anti-TSHR IgG antibody levels

DR3tg mice (n=7-10/group) were injected subcutaneously in the flank region with 15 pmol, 150 pmol and 1500 pmol of each ATX-GD-459 peptide or control peptide on days −15, −13 and −11, followed by 3 injections of 15 nmol of each ATX-GD-459 peptide or control peptide on days −8, −6 and −4 (dose escalation schedule). Starting on day −15, mice also received vehicle or MMI treatment via a subcutaneously implanted osmotic pump. Then, mice were injected intramuscularly with Ad-TSHR on two occasions on a three weekly interval (week 0 and 3). The experiment was terminated 5 weeks after the first immunization. Blood was collected before treatment and before, 2, 4 and 5 weeks after the first immunization and anti-TSHR IgG levels were analyzed by ELISA. Each dot represents data from one mouse and average±SEM are shown per group. One-way ANOVA was used to measure overall differences in anti-TSHR IgG levels. Bonferroni post-hoc testing was used and significant differences, if any, are indicated in the graphs ($*p<0.05$; $p<0.01$; $*p<0.001$; $****p<0.0001$).

Figure 12:
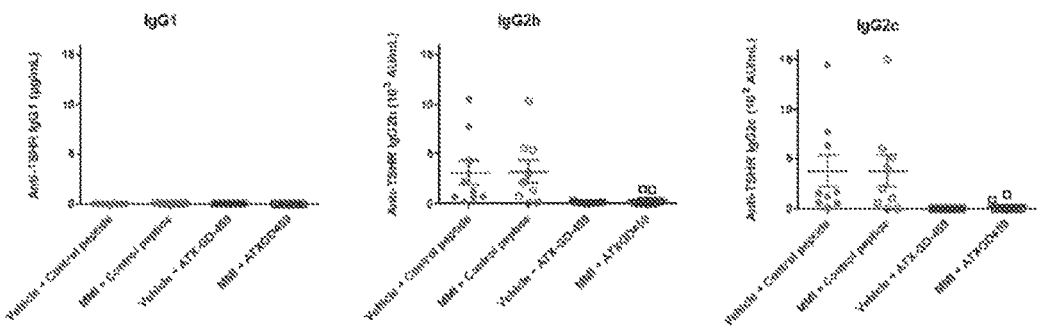

FIG. 12—ATX-GD-459 but not MMI treatment reduces anti-TSHR IgG2b and IgG2c antibody levels DR3tg mice (n=7-10/group) were injected subcutaneously in the flank region with 15 pmol, 150 pmol and 1500 pmol of each ATX-GD-459 peptide or control peptide on days −15, −13 and −11, followed by 3 injections of 15 nmol of each ATX-GD-459 peptide or control peptide on days −8, −6 and −4 (dose escalation schedule). Starting on day −15, mice also received vehicle or MMI treatment via a subcutaneously implanted osmotic pump. Then, mice were injected intramuscularly with Ad-TSHR on two occasions on a three weekly interval (week 0 and 3). The experiment was terminated 5 weeks after the first immunization. Blood was collected before treatment start and before, 2, 4 and 5 weeks after the first immunization and anti-TSHR IgG levels were analyzed by ELISA. Each dot represents data from one mouse measured at week 2 and average±SEM are shown per group. One-way ANOVA was used to measure overall differences in anti-TSHR IgG1, IgG2b and IgG2c levels. Bonferroni post-hoc testing wafs used and significant differences, if any, are indicated in the graphs ($*p<0.05$; $p<0.01$; $*p<0.001$; $****p<0.0001$).

Figure 13:
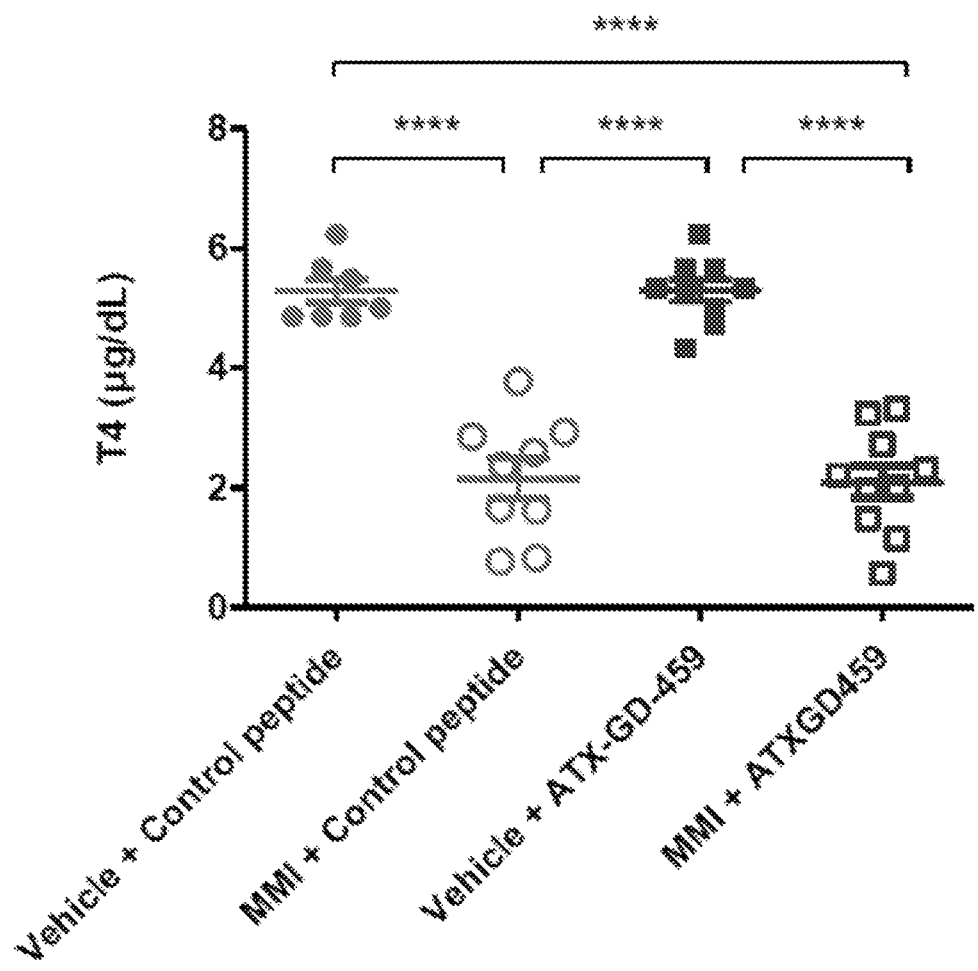

FIG. 13—MMI treatment significantly reduces serum T4 levels

DR3tg mice (n=7-10/group) were injected subcutaneously in the flank region with 15 pmol, 150 pmol and 1500 pmol of each ATX-GD-459 peptide or control peptide on days −15, −13 and −11, followed by 3 injections of 15 nmol of each ATX-GD-459 peptide or control peptide on days −8, −6 and −4 (dose escalation schedule). Starting on day −15, mice also received vehicle or MMI treatment via a subcutaneously implanted osmotic pump. Then, mice were injected intramuscularly with Ad-TSHR on two occasions on a three weekly interval (week 0 and 3). The experiment was terminated 5 weeks after the first immunization. Blood was collected before treatment and before, 2, 4 and 5 weeks after the first immunization and T4 levels were analyzed by ELISA. Each dot represents data from one mouse measured at week 5 and average±SEM are shown per group. One-way ANOVA was used to measure overall differences in T4 levels. Bonferroni post-hoc testing was used and significant differences, if any, are indicated in the graphs ($*p<0.05$; $p<0.01$; $*p<0.001$; $****p<0.0001$).

Figure 14:
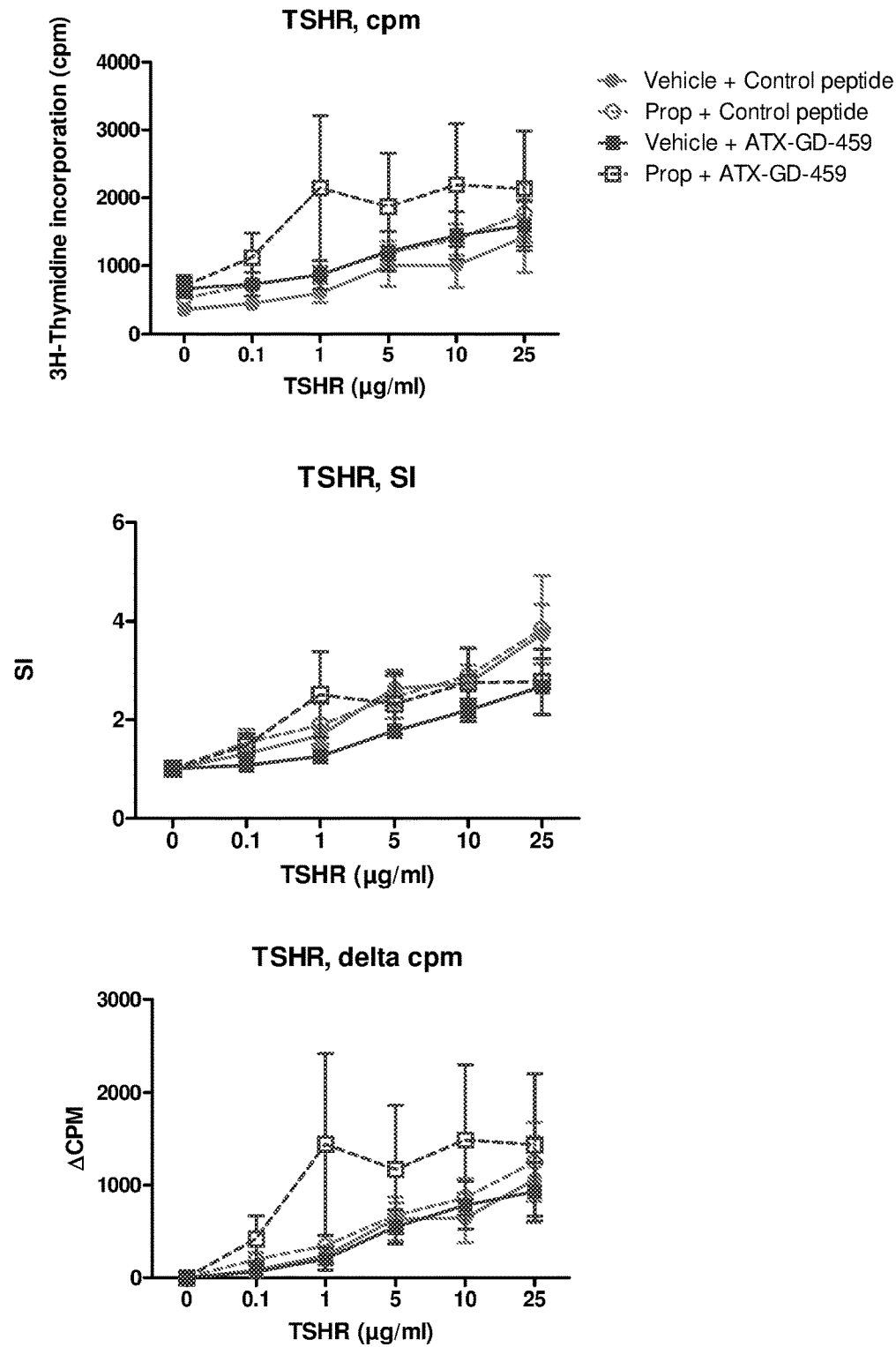

FIG. 14—TSHR-specific splenocyte proliferation in Ad-TSHR immunized DR3tg mice

DR3tg mice (n=10/group) were injected subcutaneously in the flank region with 15 pmol, 150 pmol and 1500 pmol ATXGD-459 or control treatment on days −15, −13 and −11, followed by 3 injections of 15 nmol ATX-GD-459 or control treatment on days −8, −6 and −4 (dose escalation schedule). Starting on day −15, mice also received vehicle (filled symbols) or propranolol (open symbols) treatment via daily intraperitoneal injections. Then, mice were injected intramuscularly with 1010 Ad-TSHR on two occasions on a three weekly interval (day 0 and 3). The experiment was terminated 5 weeks after the first immunization and spleens were harvested to assess the TSHR-specific proliferation Data represent mean±standard error of the mean (SEM) of absolute counts per minute (cpm; left graph), stimulation index values (SI; middle graph) or corrected counts (Δcpm; right graph). Two-way ANOVA was used to measure overall treatment effects on T cell proliferation and Bonferonni post-hoc testing was used. Significant differences are described in the text.

Figure 15:
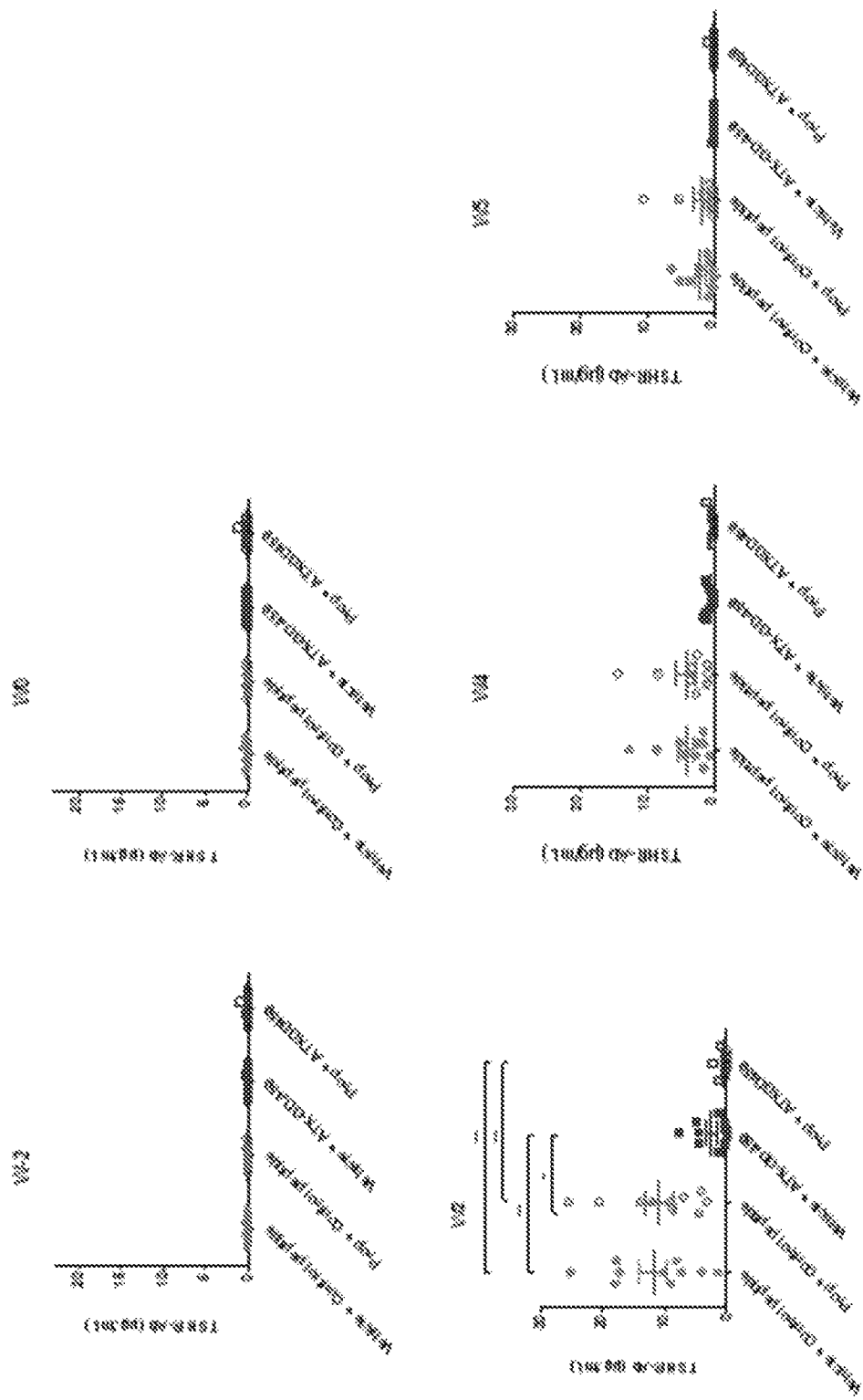

FIG. 15—ATX-GD-459 but not propranolol treatment reduces anti-TSHR IgG antibody levels DR3tg mice (n=10/group) were injected subcutaneously in the flank region with 15 pmol, 150 pmol and 1500 pmol ATXGD-459 or control treatment on days −15, −13 and −11, followed by 3 injections of 15 nmol ATX-GD-459 or control treatment on days −8, −6 and −4 (dose escalation schedule). Starting on day −15, mice also received vehicle (filled symbols) or propranolol (open symbols) treatment via daily intraperitoneal injections. Then, mice were injected intramuscularly with 1010 Ad-TSHR on two occasions on a three weekly interval (day 0 and 3). The experiment was terminated 5 weeks after the first immunization. Blood was collected before treatment and before, 2, 4 and 5 weeks after the first immunization and anti-TSHR IgG levels were analyzed by ELISA. Each dot represents data from one mouse and average±SEM are shown per group. One-way ANOVA was used to measure overall differences in anti-TSHR IgG levels. Bonferroni post-hoc testing was used and significant differences, if any, are indicated in the graphs ($*p<0.05$; $p<0.01$; $*p<0.001$; $****p<0.0001$).

Figure 16:
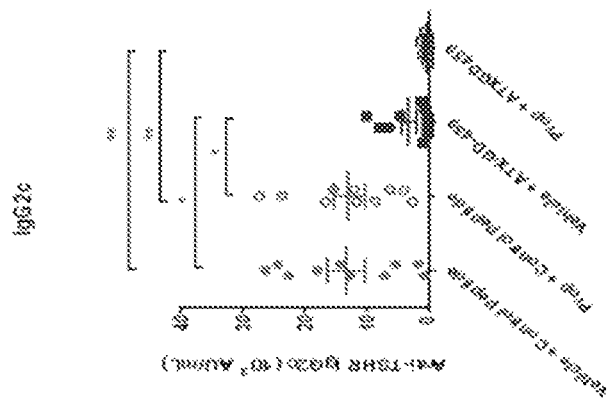
Figure 16:
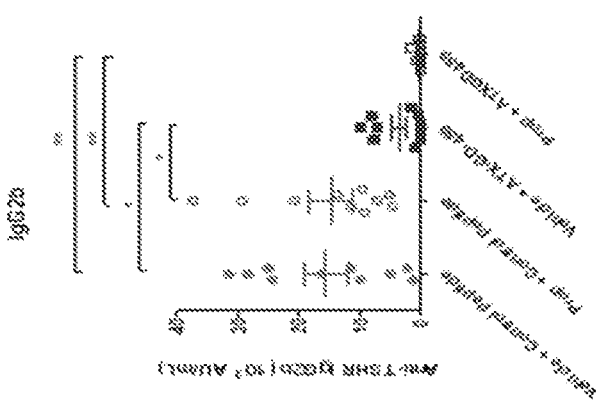
Figure 16:
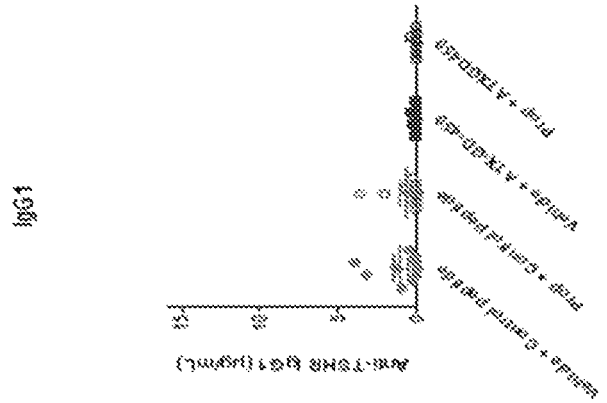

FIG. 16—ATX-GD-459 but not propranolol treatment reduces anti-TSHR IgG2b and IgG2c antibody levels DR3tg mice (n=10/group) were injected subcutaneously in the flank region with 15 pmol, 150 pmol and 1500 pmol ATXGD-459 or control treatment on days −15, −13 and −11, followed by 3 injections of 15 nmol ATX-GD-459 or control treatment on days −8, −6 and −4 (dose escalation schedule). Starting on day −15, mice also received vehicle (filled symbols) or propranolol (open symbols) treatment via daily intraperitoneal injections. Then, mice were injected intramuscularly with 1010 Ad-TSHR on two occasions on a three weekly interval (day 0 and 3). The experiment was terminated 5 weeks after the first immunization. Blood was collected before treatment and before, 2, 4 and 5 weeks after the first immunization and anti-TSHR IgG levels were analyzed by ELISA. Each dot represents data from one mouse and average±SEM are shown per group. One-way ANOVA was used to measure overall differences in anti-TSHR IgG1, IgG2b and IgG2c levels. Bonferroni post-hoc testing was used and significant differences, if any, are indicated in the graphs ($*p<0.05$; $p<0.01$; $*p<0.001$; $****p<0.0001$).

Figure 17:
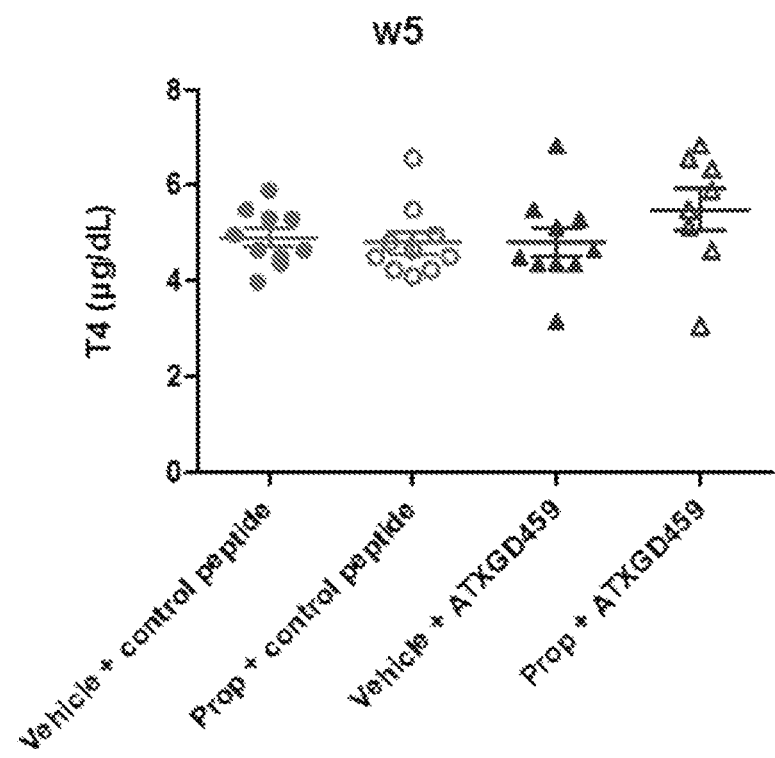

FIG. 17—Total T4 levels are not affected by propranolol or ATX-GD-459 treatment

DR3tg mice (n=10/group) were injected subcutaneously in the flank region with 15 pmol, 150 pmol and 1500 pmol ATXGD-459 or control treatment on days −15, −13 and −11, followed by 3 injections of 15 nmol ATX-GD-459 or control treatment on days −8, −6 and −4 (dose escalation schedule). Starting on day −15, mice also received vehicle (filled symbols) or propranolol (open symbols) treatment via daily intraperitoneal injections. Then, mice were injected intramuscularly with 1010 Ad-TSHR on two occasions on a three weekly interval (day 0 and 3). The experiment was terminated 5 weeks after the first immunization. Blood was collected before treatment and before, 2, 4 and 5 weeks after the first immunization and anti-TSHR IgG levels were analyzed by ELISA. Each dot represents data from one mouse measured at week 5 and average±SEM are shown per group. One-way ANOVA was used to measure overall differences in T4 levels. Bonferroni post-hoc testing was used and significant differences, if any, are indicated in the graphs ($*p<0.05$; $p<0.01$; $*p<0.001$; $****p<0.0001$).

Figure 18:
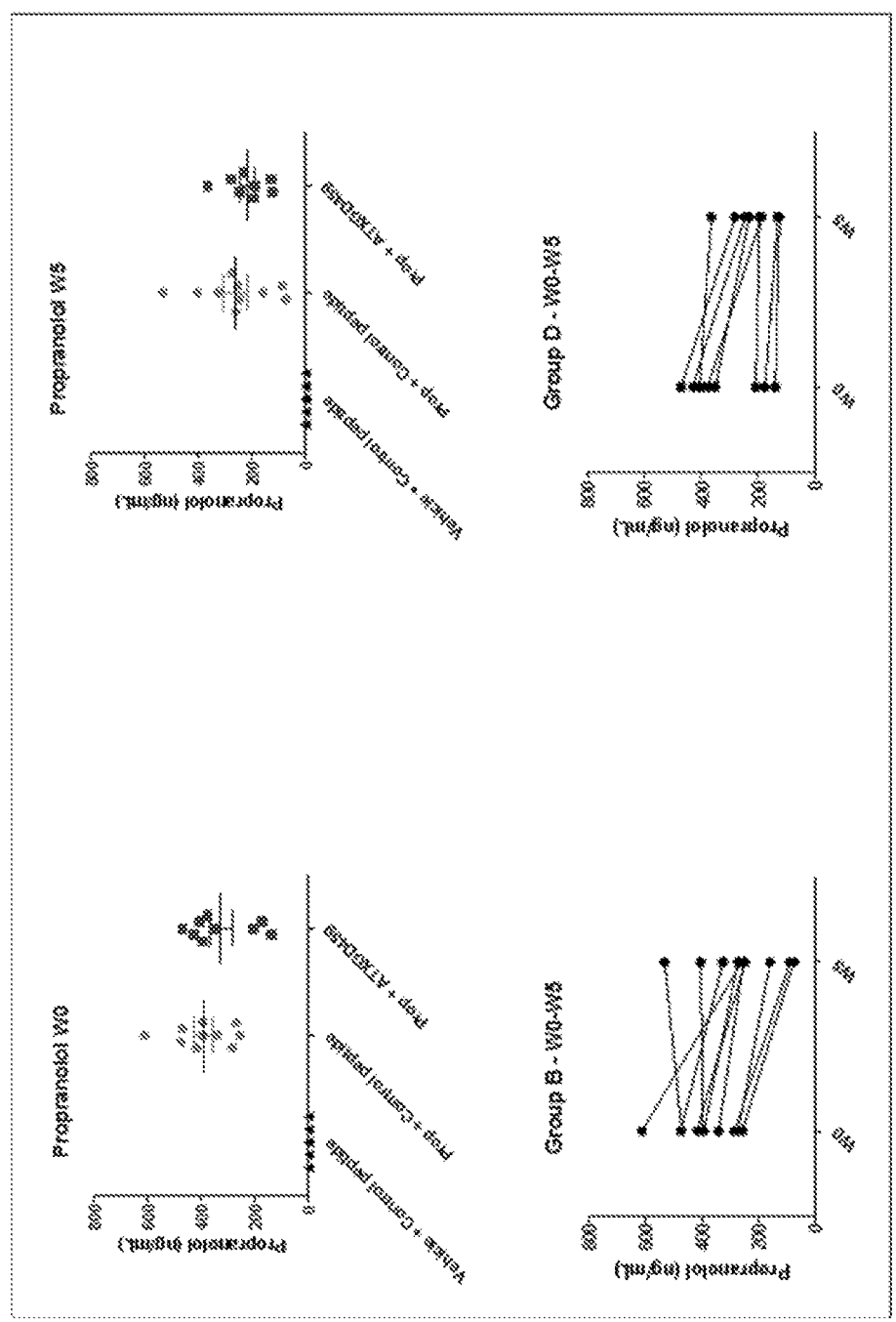

FIG. 18—Plasma levels of propranolol confirms pharmacological dose

The level of plasma propranolol was assayed in control mice and mice to who peptides and propranolol had been administered. Plasma was tested at weeks 0 and 5 and the results are shown.

Figure 19:
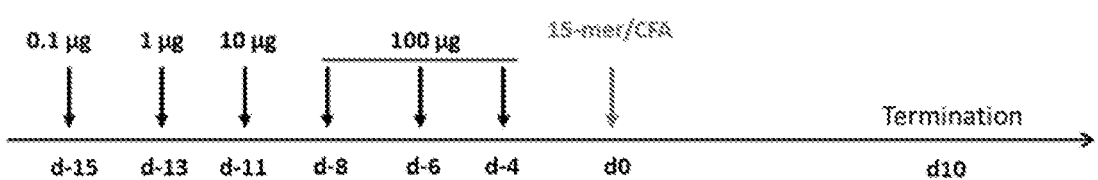

FIG. 19—Schematic T cell tolerisation protocol

Mice are injected subcutaneously in the flank region with 0.1 μg, 1 μg and 10 μg peptide on days −15, −13 and −11, followed by 3 injections at the top dose of peptide (ATX-GD-459 single peptide or cocktail) on days −8, −6 and −4 (dose escalation schedule). Top doses, and correspondingly dose escalation doses, can differ between experiments. On day 0, mice are immunised subcutaneously at the base of the tail with peptide emulsified in Complete Freund's adjuvant (CFA). The experiment is terminated 10 days after immunisation to measure the proliferation of lymph node (LN) cells and splenocytes upon TSHR or peptide re-stimulation.

Figure 20:
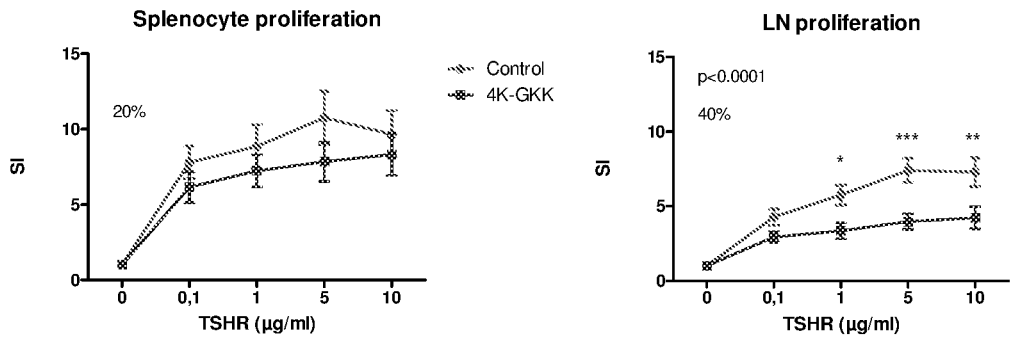
Figure 20:
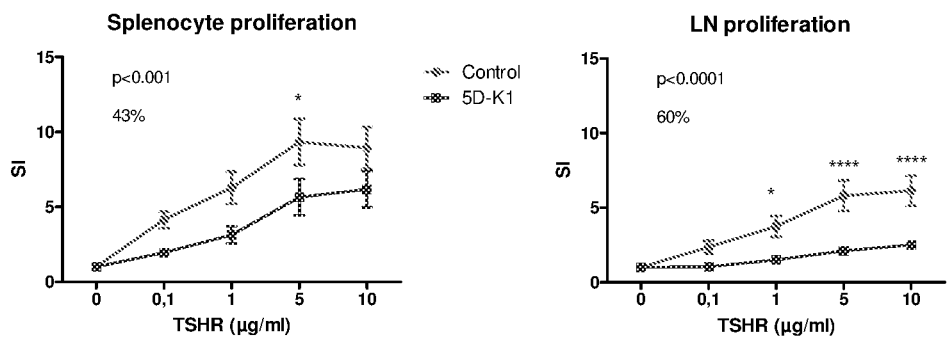
Figure 20:
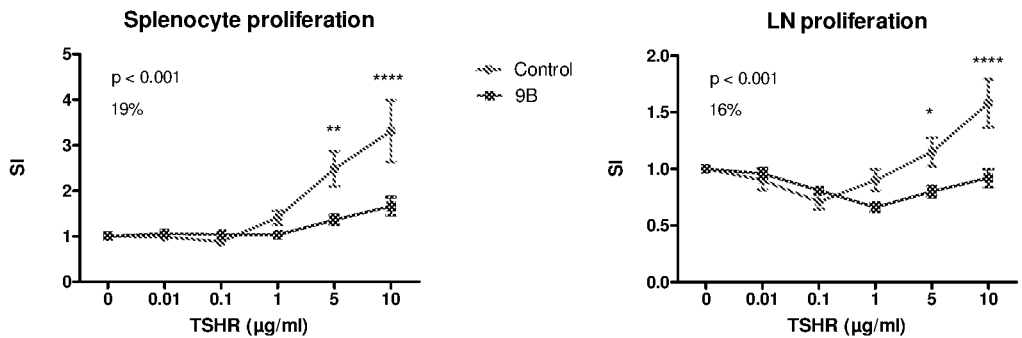
Figure 20:
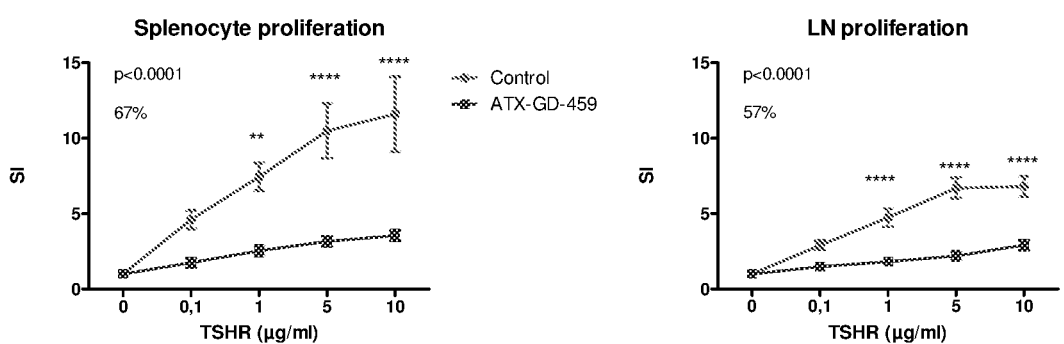

FIG. 20—ATX-GD-459 treatment efficaciously reduces TSHR-induced proliferation in HLA-DR3 mice (A) HLA-DR4 mice were pretreated with RNB-4K-GKK or PBS (n=10/group) according to the dose escalation schedule with 100 μg top dose; (B) HLA-DR3 mice were pretreated with RNB-5D-K1 or HIP-16E (HLA-DR3 binding control peptide) (n=10/group) according to the dose escalation schedule with 100 μg top dose; (C) HLA-DR3 mice were pretreated with RNB-9B or PBS (n=10/group) according to the dose escalation schedule with 33 μg top dose. Animals received an immunisation of parental peptide in CFA and after 10 days, LN and spleens were harvested to assess the TSHR-specific proliferation. Data represent mean±standard error of the mean (SEM) of stimulation index (SI) values for the control-treated mice and peptide-treated mice. Two-way ANOVA was used to measure overall treatment effects on T cell proliferation and p-values are written in the graphs. Bonferonni post-hoc testing was used and significant differences are indicated in the graphs ($*p<0.05$; $p<0.01$; $*p<0.001$: $****p<0.0001$). The average percentage reduction in T cell proliferation induced by peptide-treatment is shown in the graph. SI, stimulation index; LN; lymph nodes.

(D) HLA-DR3 mice were pretreated with ATX-GD-459 or PBS (n=10/group) according to the dose escalation schedule with 75 μg top dose for each peptide. Animals received a 4K/5D/9B emulsified in CFA immunisation and after 10 days, LN and spleens were harvested to assess the TSHR-specific proliferation. Data represent mean±SEM of stimulation index (SI) values for the control-treated mice and peptide-treated mice. Two-way ANOVA was used to measure overall treatment effects on T cell proliferation and p-values are written in the graphs. Bonferonni post-hoc testing was used and significant differences are indicated in the graphs ($*p<0.05$; $p<0.01$; $*p<0.001$: $****p<0.0001$). The average percentage reduction in T cell proliferation induced by peptide-treatment is shown in the graph. SI, stimulation index; LN; lymph nodes.

Figure 21:
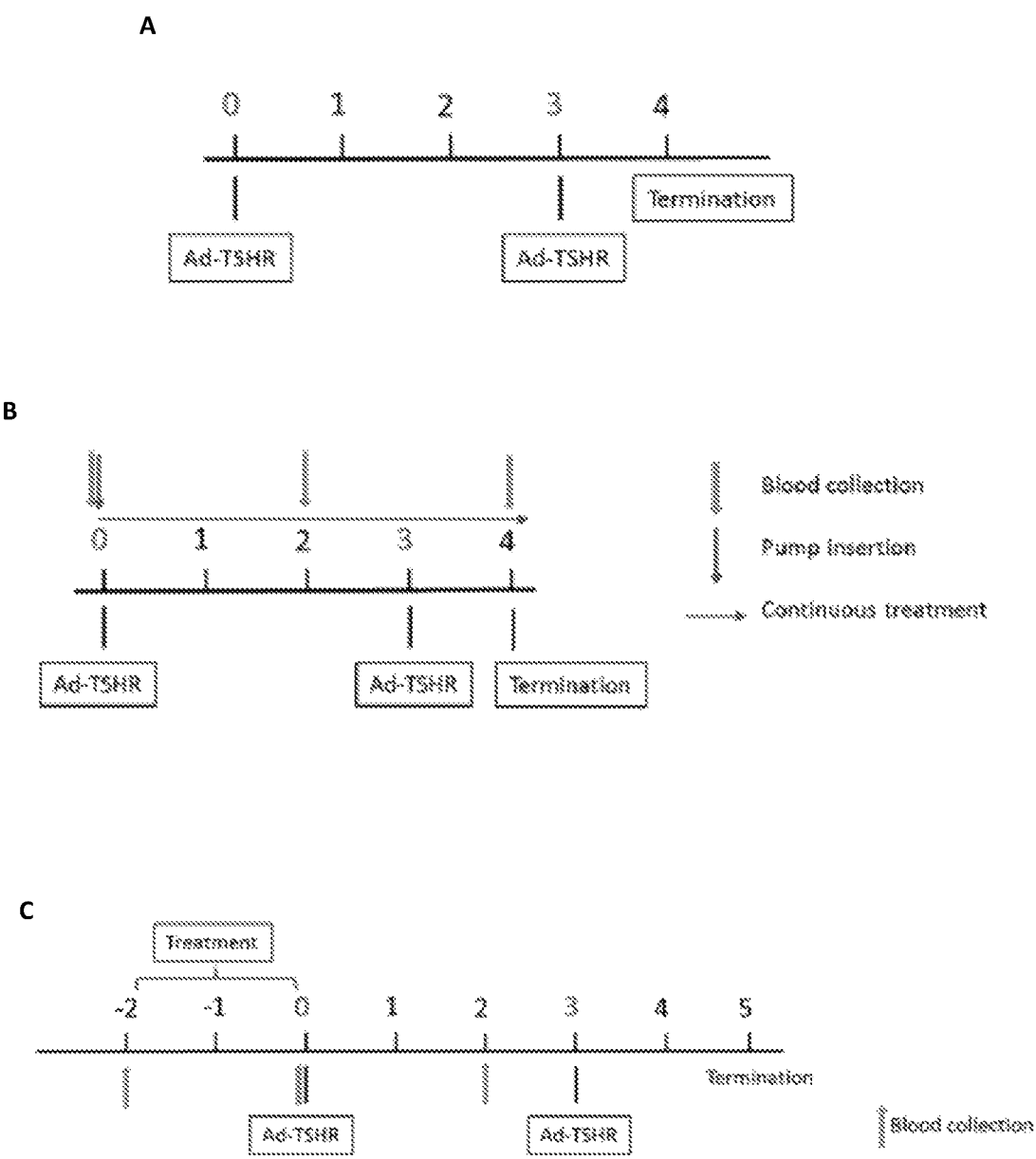

FIG. 21—Schematic overview of adenoviral Graves' disease model and validation (A) Mice were immunised via intramuscular immunisation with adenoviral vectors expressing the TSHR-A subunit (Ad-TSHR) or δ-galactosidase (Ad-LacZ). $10^{10}$ adenoviral particles were injected twice at a 3 weekly interval. Deviations to this protocol are indicated per experiment. Blood was collected before and 2 and 4 weeks after the first immunisation. The experiment was terminated 4 weeks after the first immunisation and blood, spleens and thyroids were collected for Graves' disease-like symptom investigation. (B) Mice were immunised with Ad-TSHR on two occasions on a three weekly interval (week 0 and 3). Treatment started via subcutaneous pump insertion on the day of the first immunisation and continued for 4 weeks until the end of the experiment. Blood was collected before and 2 and 4 weeks after the first immunisation. Mice were euthanized 4 weeks after the first immunisation to obtain blood and spleen samples. (C) Mice were injected subcutaneously in the flank region with 0.1 μg, 1 μg and 10 μg peptide on days −15, −13 and −11, followed by 3 injections of 100 μg peptide on days −8, −6 and −4 (dose escalation schedule). Then, mice were injected intramuscularly with Ad-TSHR or Ad-LacZ on two occasions on a three weekly interval (week 0 and 3). Blood was collected before treatment and before and 2 and 5 weeks after the first immunisation. Mice were euthanized 5 weeks after the first immunisation to obtain blood and spleen samples.

Figure 22:
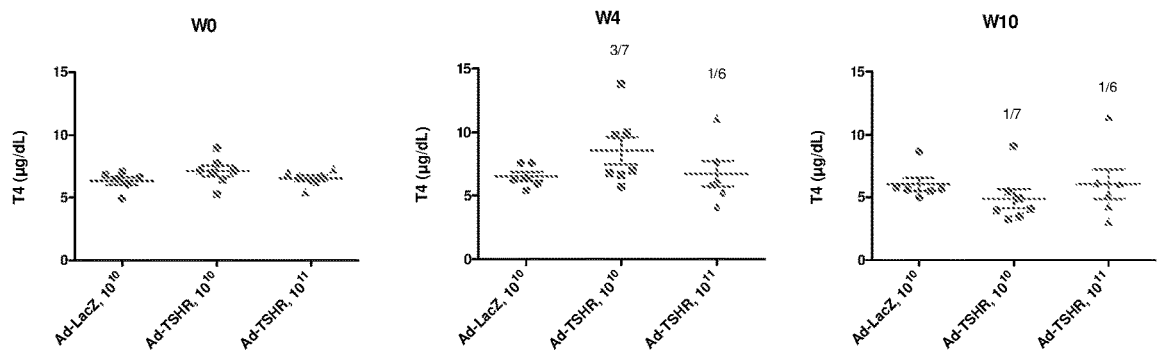
Figure 22:
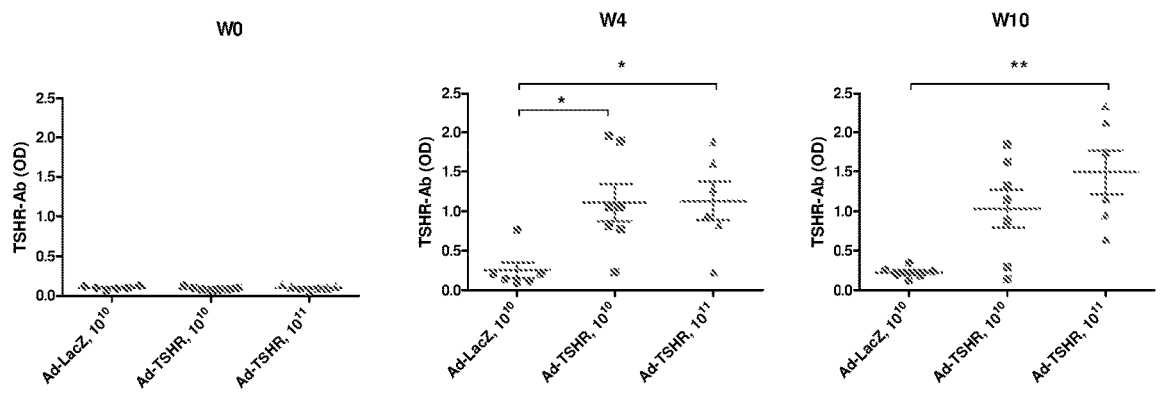

FIG. 22—Evolution of T4 and anti-TSHR IgG levels over time in BALB/c mice upon Ad-TSHR immunisation BALB/c mice (n=6-7/group) were immunised via intramuscular immunisation with $10^{10}$ or $10^{11}$ adenoviral vectors expressing the TSHR-A subunit (Ad-TSHR) or β-galactosidase (Ad-LacZ). $10^{10}$ or $10^{11}$ adenoviral particles were injected three times at a 3 weekly interval (week 0, 3 and 6). Serum was collected before and 4 and 10 weeks after the first immunisation. (A) T4 levels analyzed by ELISA. Each dot represents data from one mouse and average±SEM are shown per group. Numbers of hyperthyroid mice are indicated in the graphs. In line with published data, the cut-off for hyperthyroidism was defined as mean±2 standard deviation of the normal range murine T4 levels in Ad-LacZ immunised control mice. (B) anti-TSHR IgG levels analyzed by ELISA. Each dot represents data from one mouse and average±SEM are shown per group. One-way ANOVA was used to measure overall differences in anti-TSHR IgG levels. Bonferroni post-hoc testing was used and significant differences are indicated in the graphs (*p<0.05; p<0.01; *p<0.001; ****p<0.0001).

Figure 23:
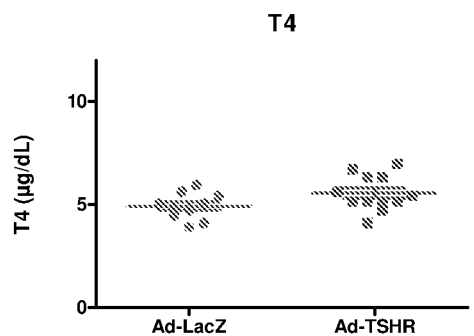
Figure 23:
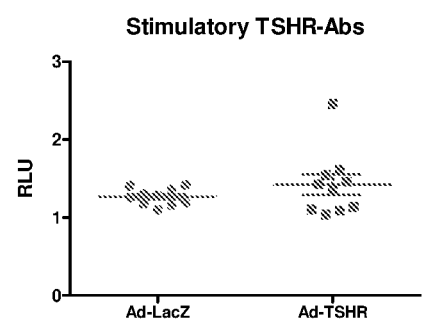
Figure 23:
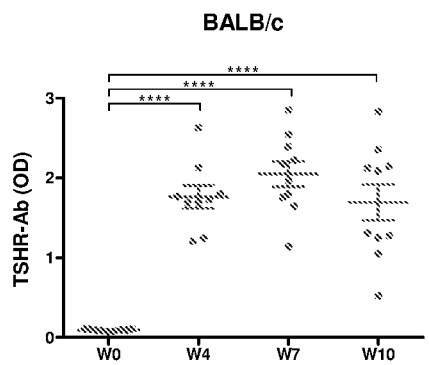
Figure 23:
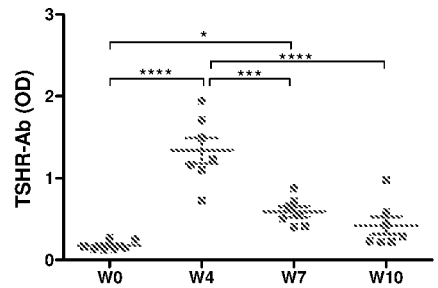
Figure 23:
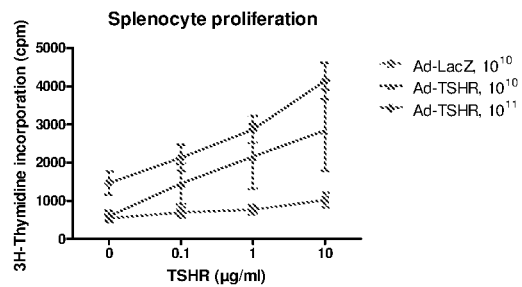
Figure 23:
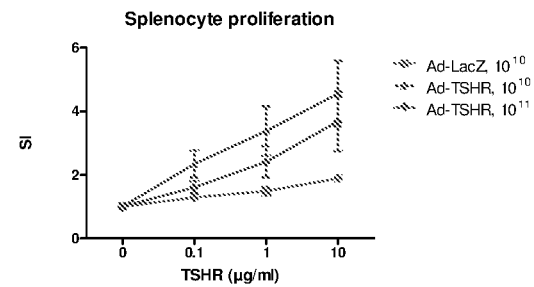

FIG. 23—Evolution of T4, stimulatory TSHR-antibodies and anti-TSHR antibody titers over time in DR3tg mice upon Ad-TSHR immunisation (A) DR3tg mice were immunised via intramuscular immunisation with $10^9$ adenoviral vectors expressing the TSHR-A subunit (Ad-TSHR) (n=10) or β-galactosidase (Ad-LacZ) (n=12). Adenoviral particles were injected twice at a 3 weekly interval (week 0 and 3). Serum was collected before and 2 and 4 weeks after the first immunisation and T4 levels were analyzed by ELISA. Each dot represents data from one mouse at week 4 and average±SEM are shown per group. Mann-Whitney test was used to measure differences in T4 levels and significant differences are indicated in the graphs (*p<0.05; p<0.01; *p<0.001; ****p<0.0001). Results are representative for more than 3 independent experiments.

(B) DR3tg mice (n=10/group) were immunised via intramuscular immunisation with $10^9$ adenoviral vectors expressing the TSHR-A subunit (Ad-TSHR) or β-galactosidase (Ad-LacZ). Adenoviral particles were injected twice at a 3 weekly interval (week 0 and 3). Serum was collected before and 2 and 4 weeks after the first immunisation and T4 levels were analyzed via the CHO luciferase reporter gene assay. Each dot represents data from one mouse at week 4 and average±SEM are shown per group. Mann-Whitney test was used to measure differences in stimulatory TSHR-antibody levels and significant differences are indicated in the graphs (*p<0.05; p<0.01; *p<0.001; ****p<0.0001). Results are representative for more than 3 independent experiments. RLU, relative light units (light emission of stimulated cells/light emission of non-stimulated cells).

(C) BALB/c mice (n=10; left panel) and DR3tg mice (n=7; right panel) were immunised via intramuscular immunisation with $10^{10}$ adenoviral vectors expressing the TSHR-A subunit (Ad-TSHR). Adenoviral particles were injected three times at a 3 weekly interval (week 0, 3 and 6). Serum was collected before and 4, 7 and 10 weeks after the first immunisation and anti-TSHR IgG levels were analysed by ELISA. Each dot represents data from one mouse and average±SEM are shown per group. One-way ANOVA was used to measure overall differences in anti-TSHR IgG levels. Bonferroni post-hoc testing was used and significant differences are indicated in the graphs (*p<0.05; p<0.01; *p<0.001; ****p<0.0001).

(D) DR3tg mice were immunised via intramuscular immunisation with $10^{10}$ or $10^{11}$ adenoviral vectors expressing the TSHR-A subunit (Ad-TSHR) or $10^{10}$ adenoviral vectors expressing β-galactosidase (Ad-LacZ). Adenoviral particles were injected three times at a 3 weekly interval (week 0, 3 and 6). After 10 weeks, spleens were collected and TSHR-induced splenocyte proliferation was measured by tritiated thymidine incorporation. Results are shown as mean±SEM per group. Cpm, counts per minute; SI, stimulation index.

Figure 24:
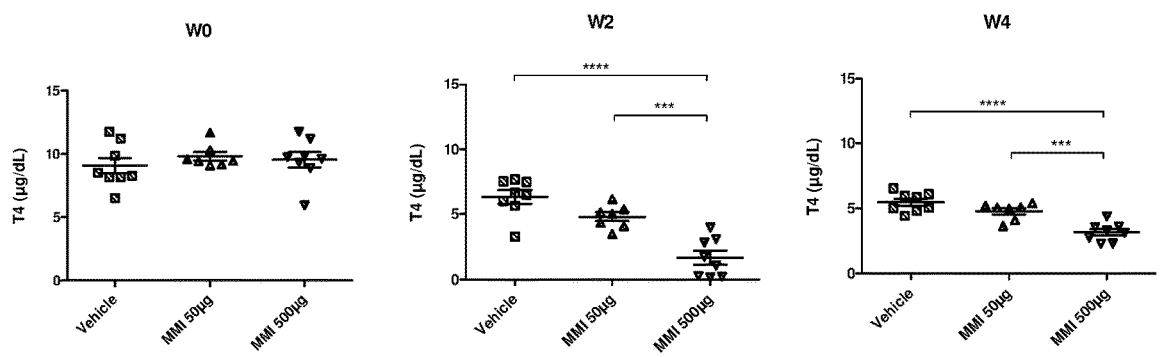
Figure 24:
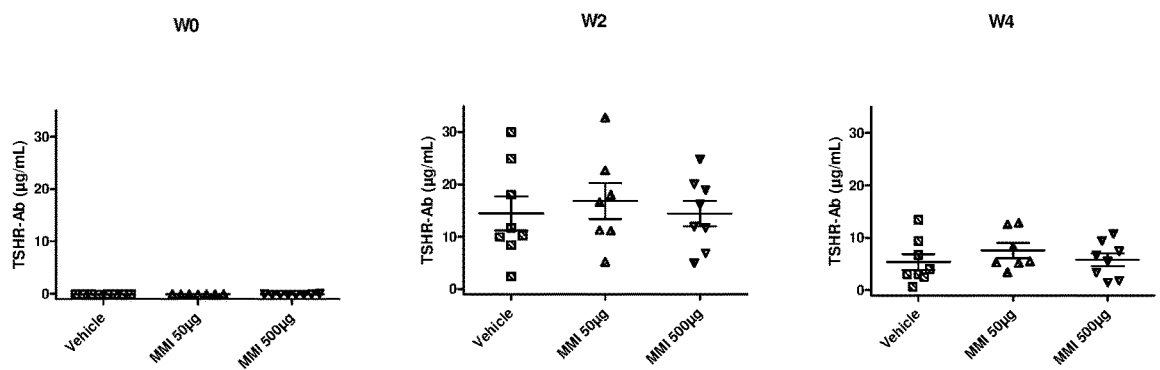

FIG. 24—Effect of methimazole treatment on T4 and anti-TSHR levels in DR3tg mice following Ad-TSHR immunisation DR3tg mice (n=7-8/group) were immunised with Ad-TSHR at week 0 and week 3. Methimazole treatment (50 or 500 μg/mouse/day) or vehicle treatment was administrated via subcutaneous pump insertion starting on the day of the first immunisation and continued for 4 weeks until the end of the experiment. Serum was collected before and 2 and 4 weeks after the first immunisation. (A) T4 levels were analysed by ELISA. Each dot represents data from one mouse and average±SEM are shown per group. One-way ANOVA was used to measure overall differences in T4 levels. Bonferroni post-hoc testing was used and significant differences are indicated in the graphs (*p<0.05; p<0.01; *p<0.001; ****p<0.0001). (B) anti-TSHR IgG levels were analysed by ELISA. Each dot represents data from one mouse and average±SEM are shown per group. One-way ANOVA was used to measure overall differences in anti-TSHR IgG levels. Bonferroni post-hoc testing was used and significant differences are indicated in the graphs (*p<0.05; p<0.01; *p<0.001; ****p<0.0001).

Figure 25:
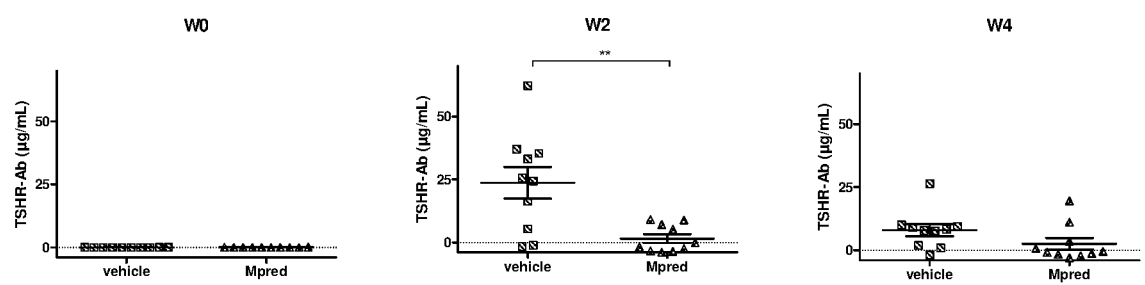

FIG. 25—Anti-TSHR IgG levels are reduced by methylprednisolone treatment

DR3tg mice (n=10/group) were immunised with $10^{10}$ Ad-TSHR at week 0 and week 3. Methylprednisolone (Mpred) treatment (7 mg/kg/day) or vehicle treatment was administrated via subcutaneous pump insertion starting 3 days prior to the first immunisation and continued for 4 weeks until the end of the experiment. Serum was collected before and 2 and 4 weeks after the first immunisation and anti-TSHR IgG levels were analysed by ELISA. Each dot represents data from one mouse and average±SEM are shown per group. Mann-Whitney test was used to measure differences in anti-TSHR IgG levels and significant differences are indicated in the graphs (*p<0.05; p<0.01; *p<0.001; ****p<0.0001).

Figure 26:
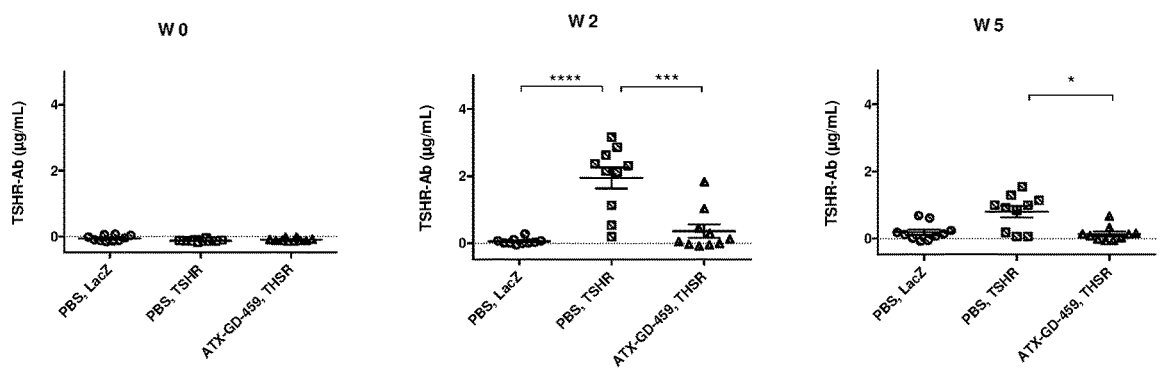

FIG. 26—ATX-GD-459 treatment reduces anti-TSHR antibody levels

DR3tg mice (n=10/group) were injected subcutaneously in the flank region with 0.1 μg, 1 μg and 10 μg ATX-GD-459 or control treatment on days −15, −13 and −11, followed by 3 injections of 100 μg ATX-GD-459 or control treatment on days −8, −6 and −4 (dose escalation schedule). Then, mice were injected intramuscularly with Ad-TSHR or Ad-LacZ on two occasions on a three weekly interval (day 0 and 3). Blood was collected before treatment and before and 2 and 5 weeks after the first immunisation to measure anti-TSHR total IgG levels by ELISA. Each dot represent data from one mouse and group average±SEM are indicated. One-way ANOVA was used to measure overall differences in anti-TSHR IgG levels. Bonferroni post-hoc testing was used and significant differences are indicated in the graphs (*p<0.05; p<0.01; *p<0.001; ****p<0.0001).

Figure 27:
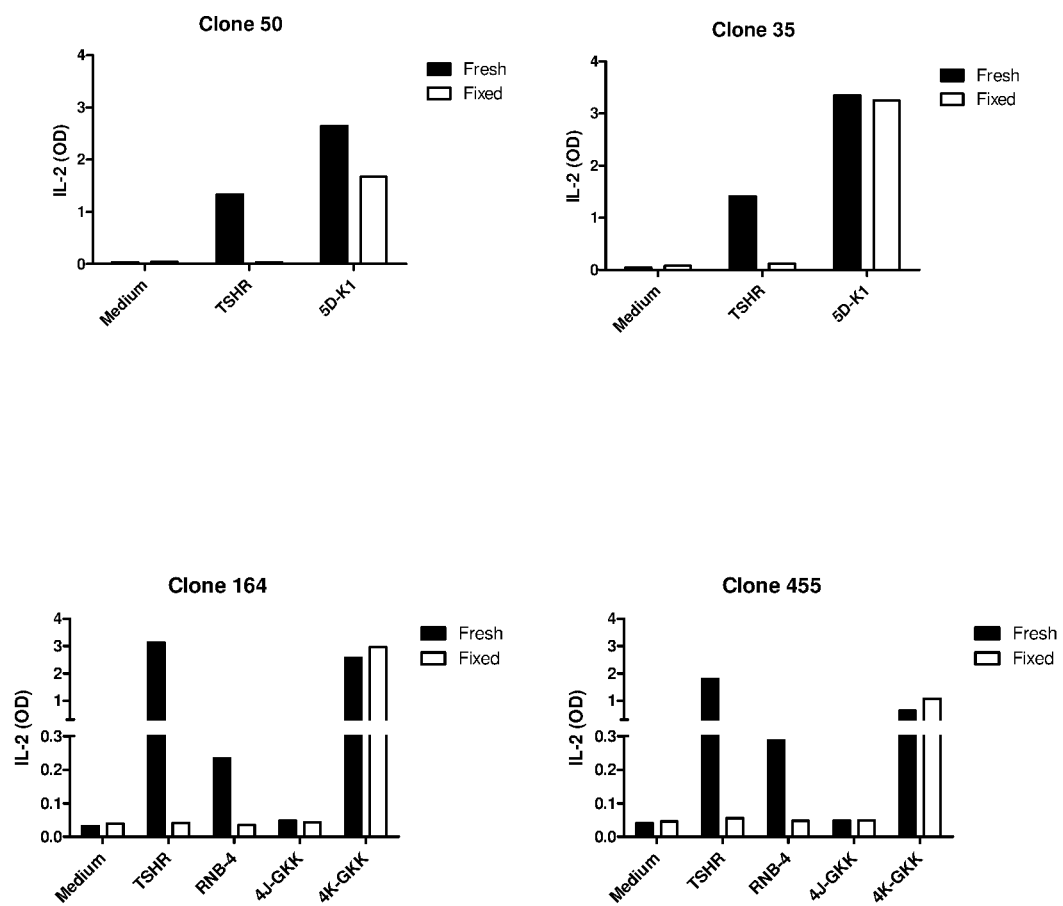

FIG. 27—APIPS assay showing hybridoma clones response to RNB-5D-K1 and RNB-4K-GKK $5 \times 10^4$ T cell hybridoma clones specific for RNB-5 (clone 50+35) or RNB-4 (clone 164+455) and TSHR were cultured in presence of TSHR and RNB-5D-K1 or RNB-4K-GKK in combination with $5 \times 10^4$ human DR3 expressing antigen presenting B cells (VAVY) (clone 50) or with DR4 expressing antigen presenting B cells (BM14) (Clone 35, 164, 455). Antigen-Presenting Cells (APC) were viable or previously fixed with 0.5% paraformaldehyde prior to addition to the culture wells. After 48 h of co-culture, the supernatants were harvested and analysed by ELISA to assess levels of IL-2 secretion. Results from representative clones are presented.

DETAILED DESCRIPTION OF THE INVENTION

The present invention provides a new and alternative therapeutic option for the prevention or suppression of production of TSHR autoantibodies, which is useful in the treatment and/or prevention of Graves' Disease. As demonstrated in Example 1 of the present application, a combination of peptides of SEQ ID NOs:1 and 2 resulting in tolerance to TSHR in a model of Graves Disease.

As such, the first aspect of the invention relates to a composition which comprises a plurality of peptides from TSHR, namely peptides of the invention as defined herein, preferably peptides of SEQ ID NO:1 and 2.

Thyroid Stimulating Hormone Receptor

Graves' disease is an autoimmune disease caused by auto-reactive T and B lymphocytes targeting the primary auto-antigen, the Thyroid Stimulating Hormone Receptor (TSHR).

TSHR is a G-protein coupled receptor on thyroid follicular cells in the thyroid gland that stimulates the production of thyroxine (T4) and triiodothyronine (T3) via a cAMP signal cascade upon binding of its ligand, the thyroid-stimulating hormone (TSH). Upon internalization, degradation and presentation of the TSHR by APCs, T cells become activated and interact with auto-reactive B cells, which in turn produce stimulating agonistic auto-antibodies directed against TSHR. The thyroid-stimulating immunoglobulins bind to the same receptor pocket as the TSH, activating the TSHR mediated signal transduction and leading to the production of excess thyroid hormone from the thyroid gland and thyroid growth.

TSHR, also known as thyrotropin receptor, is primarily expressed on thyroid epithelial cells.

The TSHR holoreceptor has 764 residues and comprises an N-terminal extracellular domain, to which TSH binds, a serpentine (or transmembrane domain) and a C-terminal intracellular domain.

TSHR comprises a large extracellular domain (418 amino acids) with highly conserved Cys residues, which facilitate the formation of an extracellular domain tertiary structure that may be important in both ligand binding and inactive receptor conformation. The extracellular domain comprises over half the total protein length and is sufficient for high-affinity ligand binding. After being transported to the cell surface the receptor molecule is subjected to intra-molecular cleavage, leading to the removal of a 50 amino acid sequence between residues 316 and 366. As a result the receptor comprises two subunits, the a subunit comprising the extracellular ligand-binding domain and the β subunit comprising the transmembrane domain and the short C-terminal sequence, bound together with disulphide bonds. In subsequent steps, the α subunit is shed, leading to an excess of ligand-binding domain deprived β subunits on the cell membrane.

Following the binding of circulating TSH to TSHR, a G-protein signalling cascade activates adenylyl cyclase and intercellular levels of cAMP rise. cAMP activates all functional aspects of the thyroid cell, including iodine pumping, thyroglobulin synthesis, iodination, endocytosis and proteolysis, thyroid peroxidase activity and hormone release.

The amino acid sequence of mature TSHR is given below (SEQ ID No. 3).

```
  1 mrpadllqlv llldlprdlg gmgcssppce chqeedfrvt ckdiqripsl ppstqtlkli
 61 ethlrtipsh afsnlpnisr iyvsidvtlq qleshsfynl skvthieirn trnltyidpd
121 alkelpllkf lgifntglkm fpdltkvyst diffileitd npymtsipvn afqglcnetl
181 tlklynngft svqgyafngt kldavylnkn kyltvidkda fggvysgpsl ldvsqtsvta
241 lpskglehlk eliarntwtl kklplslsfl hltradlsyp shccafknqk kirgileslm
301 cnessmqslr qrksvnalns plhqeyeenl gdsivgykek skfqdthnna hyyvffeeqe
361 deiigfgqel knpqeetlqa fdshydytic gdsedmvctp ksdefnpced imgykflriv
421 vwfvsllall gnvfvllill tshyklnvpr flmcnlafad fcmgmyllli asvdlythse
481 yynhaidwqt gpgcntagff tvfaselsvy tltvitlerw yaitfamrld rkirlrhaca
541 imvggwvccf llallplvgi ssyakvsicl pmdtetplal ayivfvltln ivafvivccc
601 yvkiyitvrn pqynpgdkdt kiakrmavli ftdficmapi sfyalsailn kplitvsnsk
661 illvlfypln scanpflyai ftkafqrdvf illskfgick rqaqayrgqr vppknstdiq
721 vqkvthdmrq glhnmedvye lienshltpk kqgqiseeym qtvl
```

Tolerance

T cell epitopes play a central role in the adaptive immune response to any antigen, whether self or foreign. The central role played by T cell epitopes in hypersensitivity diseases (which include allergy, autoimmune diseases and transplant rejection) has been demonstrated through the use of experimental models. It is possible to induce inflammatory or allergic diseases by injection of synthetic peptides (based on the structure of T cell epitopes) in combination with adjuvant.

By contrast, it has been shown to be possible to induce immunogenic tolerance towards particular antigens by administration of peptide epitopes in soluble form. Administration of soluble peptide has been demonstrated as an effective means of inhibiting disease in experimental autoimmune encephalomyelitis (EAE—a model for multiple sclerosis (MS)) (Metzler and Wraith (1993) Int. Immunol. 5:1159-1165; Liu and Wraith (1995) Int. Immunol. 7:1255-1263; Anderton and Wraith (1998) Eur. J. Immunol. 28:1251-1261); and experimental models of arthritis, diabetes, and uveoretinitis (reviewed in Anderton and Wraith (1998) as above). This has also been demonstrated as a means of treating an ongoing disease in EAE (Anderton and Wraith (1998) as above).

Tolerance is the failure of the immune system to respond to an antigen. Tolerance to self antigens is an essential feature of the immune system; when this is lost, autoimmune disease can result. The adaptive immune system must maintain the capacity to respond to an enormous variety of infectious agents while avoiding autoimmune attack of the self antigens contained within its own tissues. This is controlled to a large extent by the sensitivity of immature T lymphocytes to apoptotic cell death in the thymus (central tolerance). However, not all self antigens are detected in the thymus, so death of self-reactive thymocytes remains incomplete. There are thus also mechanisms by which tolerance may be acquired by mature self-reactive T lymphocytes in the peripheral tissues (peripheral tolerance). A review of the mechanisms of central and peripheral tolerance is given in Anderton et al (1999) (Immunological Reviews 169:123-137).

Graves' disease is currently believed to be caused by TSHR stimulating autoantibodies that bind to and activate the TSHR, thereby stimulating thyroid hormone synthesis and secretion, and thyroid growth. The composition of the present invention is capable of inducing tolerance to TSHR, such that when administered to a subject, it may reinstate tolerance to the TSHR self-protein and curtail the pathogenic immune response.

Apitopes

In an adaptive immune response, T lymphocytes are capable of recognising internal epitopes of a protein antigen. APCs take up protein antigens and degrade them into short peptide fragments. A peptide may bind to a major histocompatibility molecule inside the cell and be carried to the cell surface. When presented at the cell surface in conjunction with an MHC molecule, the peptide may be recognised by a T cell (via the T cell receptor (TCR)), in which case the peptide is a T cell epitope.

An epitope is thus a peptide derivable from an antigen which is capable of binding to the peptide-binding groove of an MHC molecule and being recognised by a T cell.

The minimal epitope is the shortest fragment derivable from an epitope, which is capable of binding to the peptide-binding grove of an MHC molecule and being recognised by a T cell. For a given immunogenic region, it is typically possible to generate a "nested set" of overlapping peptides which act as epitopes, all of which contain the minimal epitope but differ in their flanking regions.

By the same token, it is possible to identify the minimal epitope for a particular MHC molecule:T cell combination by measuring the response to truncated peptides. For example, if a response is obtained to the peptide comprising residues 1-15 in the overlapping library, sets which are truncated at both ends (i.e. 1-14, 1-13, 1-12 etc. and 2-15, 3-15, 4-15 etc.) can be used to identify the minimal epitope.

The present inventors have previously determined that there is a link between the capacity of a peptide to bind to an MHC molecule and be presented to a T cell without further processing, and the peptide's capacity to induce tolerance in vivo (WO 02/16410). If a peptide is too long to bind the peptide binding groove of an MHC molecule without further processing (e.g. trimming), or binds in an inappropriate conformation then it will not be tolerogenic in vivo. If, on the other hand, the peptide is of an appropriate size and conformation to bind directly to the MHC peptide binding groove and be presented to a T cell, then this peptide can be predicted to be useful for tolerance induction.

It is thus possible to investigate the tolerogenic capacity of a peptide by investigating whether it can bind to an MHC molecule and be presented to a T cell without further antigen processing in vitro.

TSHR apitopes (Antigen Processing-Independent epiTOPES) are capable of binding to an MHC molecule and stimulating a response from TSHR specific T cells without further antigen processing. Such apitopes can be predicted to cause tolerance to TSHR, following the rule-based method described in WO 02/16410.

Peptides that bind to MHC class I molecules are typically 7 to 13, more usually 8 to 10 amino acids in length. The binding of the peptide is stabilised at its two ends by contacts between atoms in the main chain of the peptide and invariant sites in the peptide-binding groove of all MHC class I molecules. There are invariant sites at both ends of the groove which bind the amino and carboxy termini of the peptide. Variations in peptide length are accommodated by a kinking in the peptide backbone, often at proline or glycine residues that allow flexibility.

Peptides which bind to MHC class II molecules are typically between 8 and 20 amino acids in length, more usually between 10 and 17 amino acids in length, and can be longer (for example up to 40 amino acids). These peptides lie in an extended conformation along the MHC II peptide-binding groove which (unlike the MHC class I peptide-binding groove) is open at both ends. The peptide is held in place mainly by main-chain atom contacts with conserved residues that line the peptide-binding groove.

In a preferred embodiment, the peptide is capable of binding to an MHC class II molecule without further processing.

Peptide

The term "peptide" is used in the normal sense to mean a series of residues, typically L-amino acids, connected one to the other, typically by peptide bonds between the α-amino and carboxyl groups of adjacent amino acids. The term includes modified peptides and synthetic peptide analogues.

The peptides may be made using chemical methods (Peptide Chemistry, A practical Textbook. Mikos Bodansky, Springer-Verlag, Berlin). For example, peptides can be synthesized by solid phase techniques (Roberge J Y et al (1995) Science 269: 202-204), cleaved from the resin, and purified by preparative high performance liquid chromatography (e.g., Creighton (1983) Proteins Structures And Molecular Principles, WH Freeman and Co, New York, N.Y.). Automated synthesis may be achieved, for example, using the ABI 43 1 A Peptide Synthesizer (Perkin Elmer) in accordance with the instructions provided by the manufacturer.

The peptide may alternatively be made by recombinant means, or by cleavage from a longer polypeptide. For example, the peptide may be obtained by cleavage from the thyrotropin receptor protein, which may be followed by modification of one or both ends. The composition of a peptide may be confirmed by amino acid analysis or sequencing (e.g., the Edman degradation procedure).

The peptides used in the present invention are as follows:

(i) all or part of the amino acid sequence KKKKYVSID-VTLQQLESHKKK (SEQ ID NO: 1), or a part thereof, or a sequence having at least 60% sequence identity to SEQ ID NO:1;

and (ii) all or part of the amino acid sequence GLKMFPDLT-KVYSTD (SEQ ID NO: 2), or a part thereof, or a sequence having at least 60% sequence identity to SEQ ID NO:2.

The peptide according to the present invention may comprise or consist of an amino acid sequence having at least 60%, 61%, 62%, 63%, 64%, 65%, 66%, 67%, 68%, 69%, 70%, 71%, 72%, 73%, 74%, 75%, 76%, 77%, 78%, 79%, 70%, 81%, 82%, 83%, 84, 85%, 86%, 87%, 88%, 89%, 90%, 91%, 92%, 93%, 94%, 95%, 96%, 97%, 98%, 99% or 100% identity with a peptide of SEQ ID NOs: 1 or 2. In one aspect the peptide has at least 70%, 75%, 80%, 85%, 90%, 95% or 100% sequence identity to SEQ ID NOs:1 or 2.

In a preferred aspect the peptides comprise SEQ ID NOs:1 and 2. In a further preferred aspect the peptides consist of SEQ ID NOs:1 and 2.

Sequence identity may be assessed by any convenient method. However, for determining the degree of sequence identity between sequences, computer programs that make multiple alignments of sequences are useful, for instance Clustal W (Thompson et al., (1994) Nucleic Acids Res., 22: 4673-4680). Programs that compare and align pairs of sequences, like ALIGN (Myers et al., (1988) CABIOS, 4: 1-17), FASTA (Pearson et al., (1988) PNAS, 85:2444-2448; Pearson (1990), Methods Enzymol., 183: 63-98) and gapped BLAST (Altschul et al., (1997) Nucleic Acids Res., 25: 3389-3402) are also useful for this purpose. Furthermore, the Dali server at the European Bioinformatics institute offers structure-based alignments of protein sequences (Holm (1993) J. Mol. Biol., 233: 123-38; Holm (1995) Trends Biochem. Sci., 20: 478-480; Holm (1998) Nucleic Acid Res., 26: 316-9).

Multiple sequence alignments and percent identity calculations may be determined using the standard BLAST parameters, (using sequences from all organisms available, matrix Blosum 62, gap costs: existence 11, extension 1).

Alternatively, the following program and parameters may be used: Program: Align Plus 4, version 4.10 (Sci Ed Central Clone Manager Professional Suite). DNA comparison: Global comparison, Standard Linear Scoring matrix, Mismatch penalty=2, Open gap penalty=4, Extend gap penalty=1. Amino acid comparison: Global comparison, BLOSUM 62 Scoring matrix.

Thus included in the scope of the invention are variants of the stated or given sequences, as long as the variant retains the functional activity of the parent i.e. the variants are functionally equivalent, in other words they have or exhibit an activity of the parent peptide as defined herein. Such variants may comprise amino acid substitutions, additions or deletions (including truncations at one or both ends) of the parent sequence e.g. of one or more e.g. 1 to 14 amino acids.

Also included are functionally-equivalent derivatives in which one or more of the amino acids are chemically derivitised, e.g. substituted with a chemical group.

Thus, the peptides of the invention can comprise parts or fragments of SEQ ID NOs:1-3, provided that the peptide retains the required activity. Fragments or parts of SEQ ID NOs:1-3 may for example be from 6 to 14 residues in length, e.g. 6, 7, 8, 9, 10, 11, 12 or 13 residues in length.

The peptide of the present invention may comprise between 8 and 30 amino acids, for example 8 to 25 amino acids, 8 to 20 amino acids, 8 to 15 amino acids or 8 to 12 amino acids. In one aspect the peptide of the present invention may thus be 8, 9, 10, 11, 12, 13, 14, 15, 16, 17, 18, 19, 20, 21, 22, 23, 24, 25, 26, 27, 28, 29 or 30 amino acids in length.

The TSHR peptides may be in the form of a composition, preferably a pharmaceutical composition.

TSHR peptides may be formulated into the composition as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric and maleic acid. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine and procaine.

Combination

The present inventors have found that, surprisingly, the peptides and/or composition according to the present invention can be administered in combination with other therapies used in the treatment or management of Graves' Disease, whilst maintaining therapeutic effects of both the peptides/composition of the invention and the other therapeutic agent.

As such, in one aspect the peptides or composition of the invention may be combined with a further therapeutic agent that is used in the treatment of prevention of Graves' Disease.

For example, the peptides or composition may be combined with an antithyroid agent, or a β-blocker.

As demonstrated in Example 2, administering a peptide of SEQ ID NO:1 and SEQ ID NO:2 in combination with an antithyroid agent did not affect the reduction in anti-TSHR antibody production due to the TSHR peptides, nor was the antithyrotic action (measured by T4 production) reduced, i.e. both therapeutic actions were maintained. Similar results were also achieved for a combination of the composition according to the invention in combination with a β-blocker. As such, the present inventors have demonstrated that the peptides according to the present invention can be used in combination with existing therapies for the treatment and management of Graves' Disease.

The combination according to the invention is advantageous in that it facilitates reduction of an autoimmune response in Graves' Disease, i.e. the underlying mechanism, whilst allowing treatment or management of the symptoms of Graves' Disease at the same time.

An "antithyroid agent" is a hormone antagonist acting upon thyroid hormones. Antithyroid agents are used in the treatment of Graves' Disease. Antithyroid agents are given to Graves' Disease patients for their inhibitory effect on thyroid hormone synthesis, thereby directly reducing their thyroxine (T4) levels.

In one embodiment the antithyroid agent is selected from carbimazole, methimazole (MMI), propylthiouracil (PTU) and potassium perchlorate. In a preferred embodiment the antithyroid agent is methimazole (MMI).

β-blockers are given to Graves' Disease patients to combat the β-adrenergic consequences of hyperthyroidism (without treating the immunologic compounds of the disease).

β-blockers are a class of drugs that are used for the management of cardiac arrhythmias. Beta blockers block the action of endogenous catecholamines epinephrine (adrenaline) and norepinephrine (noradrenaline)—in particular on adrenergic beta receptors, of the sympathetic nervous system.

β-blockers according to the invention include: Propranolol, Bucindolol, Carteolol, Carvedilol, Labetalol, Nadolol, Oxprenolol, Penbutolol, Pindolol, Sotalol and Timolol.

In a preferred embodiment the β-blocker is propranolol.

Pharmaceutically acceptable salts of β-blockers may be used. In a preferred embodiment the β-blocker is propranolol hydrochloride.

Suitable doses of the antithyroid agent and β-blocker can be determined by one skilled in the art. By way of example, an antithyroid agent may be administered in a dose of between 10 and 1000 µg, e.g. between 20 and 900, 30 and 800, 40 and 700, 50 and 600, 60 and 500, 70 and 400, 80 and 300, or 90 and 200 µg. In a preferred embodiment a dose of between 300 and 700 µg is administered, e.g. about 500 µg and preferably 500 µg.

In a preferred embodiment the antithyroid agent is administered daily, e.g. every 20-28 hours, preferably every 24 hours.

The antithyroid agent may be administered via any suitable route, and this will be known to one skilled in the art. In a preferred embodiment the antithyroid agent is administered subcutaneously.

The β-blocker may be administered at a dose of, for example, between 1 and 100 mg/kg, e.g. between 5 and 90, 10 and 80, 15 and 75, 20 and 70, 25 and 60, 30 and 55, 35 and 50, and 40 and 45 mg/kg. In a preferred embodiment the β-blocker is administered at a dose of 5-20 mg/kg, preferably about 10 mg/kg, more preferably 10 mg/kg.

In a preferred embodiment the β-blocker is administered daily, e.g. every 20-28 hours, preferably every 24 hours.

The β-blocker may be administered via any suitable route, and this will be known to one skilled in the art. In a preferred embodiment the β-blocker is administered intraperitoneally.

In one embodiment the peptides or composition according to the invention are administered at the same time as the antithyroid agent and/or β-blocker. In an alternative embodiment the peptides or composition according to the invention are administered at a different time to the antithyroid agent and/or β-blocker.

In one aspect the invention the subject to whom the peptides/composition is administered (or to whom it is intended to administer) is already taking the antithyroid agent and/or β-blocker. As such, the invention encompasses the use of the invention wherein the subject is, or has previously been, taking an antithyroid agent and/or β-blocker.

In a further aspect of the invention the subject is not, and/or has not been, taking any therapeutic agents for Graves' Disease.

In one aspect of the invention discussed herein, as a first step a subject is identified who has or is at risk of developing, Graves' Disease.

The peptides or composition according to the present invention may be for prophylactic or therapeutic use.

When administered for prophylactic use, the peptides or composition may reduce or prevent the generation of an immune response to TSHR. The level of immune response is less than would be obtained if the patient had not been treated with the composition. The term "reduce" indicates that a partial reduction in immune response is observed, such as a 50%, 70%, 80% or 90% reduction in the response that would have been observed if the patient had not been treated with the composition (or in the response observed in an untreated patient over the same time-period). The term "prevent" indicates that no appreciable immune response to TSHR is observed.

When administered for therapeutic use, the peptides or composition may suppress an already on-going immune response to TSHR. The term "suppress" indicates a reduction in the level of an on-going immune response, compared to the level before peptide treatment, or the levels which would have been observed at the same time point had the treatment not been given.

Treatment with the peptides or composition of the present invention may cause a reduction in level of any or all of the following:
i) TSHR autoantibodies
ii) CD4+ T cells specific for TSHR
iii) B cells secreting TSHR autoantibodies.

Detection of all of the factors can be carried out by techniques known in the art, such as ELISA, flow cytometry etc.

Treatment with the peptides or composition of the present invention may also or alternatively cause anergy in CD4+ T cells specific for TSHR. Anergy can be detected by, for example, subsequent challenge with TSHR in vitro.

Formulation

The peptides or composition may by prepared as an injectable, either as liquid solution or suspension; solid form suitable for solution in, or suspension in, liquid prior to injection may also be prepared. The preparation may also be emulsified, or the peptides encapsulated in liposomes. The active ingredients may be mixed with excipients which are pharmaceutically acceptable and compatible with the active ingredient. Suitable excipients are, for example, water, saline (for example, phosphate-buffered saline), dextrose, glycerol, ethanol, or the like and combinations thereof.

In addition, if desired, the composition may contain minor amounts of auxiliary substances such as wetting or emulsifying agents and/or pH buffering agents. Buffering salts include phosphate, citrate, acetate. Hydrochloric acid and/or sodium hydroxide may be used for pH adjustment. For stabilisation, disaccharides may be used such as sucrose or trehalose.

In the composition, the relative ratio of the peptides (RNB-5D-K1 and RNB-9B) may be approximately 1:1. Alternatively the relative ratios of each peptide may be altered, for example, to focus the tolerogenic response on a particular subset of autoreactive T cells or if it is found that one peptide works better than the others in particular HLA types.

After formulation, the peptides or composition may be incorporated into a sterile container which is then sealed and stored at a low temperature, for example 4° C., or it may be freeze-dried.

Conveniently the peptides or composition are prepared as a lyophilised (freeze-dried) powder. Lyophilisation permits long-term storage in a stabilised form. Lyophilisation procedures are well known in the art, see for example http COLON-SLASH-SLASH www.devicelink.com/ivdt/archive/97/01/006.html. Bulking agents are commonly used prior to freeze-drying, such as mannitol, dextran or glycine, or sugars such as trehalose.

The peptides or composition may be administered in a convenient manner such as by the oral, intravenous (where water soluble), intramuscular, subcutaneous, sublingual, intranasal, intradermal or suppository routes or implanting (e.g. using slow release molecules).

The peptides or composition may advantageously be administered via intranasal, subcutaneous or intradermal routes.

The method, peptides and composition of the invention may be used to treat a human subject. Typically, a physician will determine the actual dosage which will be most suitable for an individual subject and it will vary with the age, weight and response of the particular patient.

The peptides and composition of the invention may be used to treat a human subject. The subject may have Graves' disease. The subject may have TSHR autoantibodies.

The subject may be an HLA-haplotype which is associated with a predisposition to develop inhibitory THSR autoantibodies. The subject may express HLA-DR3 or HLA-DR4. Methods for determining the HLA haplotype of an individual are known in the art.

In a preferred embodiment a "dose escalation" protocol may be followed, where a plurality of doses is given to the patient in ascending concentrations. Such an approach has been used, for example, for phospholipase A2 peptides in immunotherapeutic applications against bee venom allergy (Müller et al (1998) J. Allergy Clin Immunol. 101:747-754 and Akdis et al (1998) J. Clin. Invest. 102:98-106).

Kit

Conveniently, the two TSHR peptides may be administered together, in the form of a mixed composition or cocktail. However, there may be circumstances in which it is preferable to provide the peptides separately in the form of a kit, for simultaneous, separate, sequential or combined administration.

For example, the kit may comprise the two peptides in separate containers. The contents of the containers may or may not be combined prior to administration.

The kit may also comprise mixing and/or administration means (for example a vapouriser for intranasal administration; or a syringe and needle for subcutaneous/intradermal dosing). The kit may also comprise instructions for use.

The pharmaceutical composition or kit of the invention may be used to treat and/or prevent a disease.

In particular, the composition/kit may be used to suppress or prevent the production of TSHR autoantibodies in vivo. The composition/kit may be used to treat and/or prevent Graves' disease in a subject.

Animal Model

Present animal models of Graves' disease are associated with various shortcomings. For example, the currently used animal models do not develop symptoms or features which are relevant to Graves' disease. In addition, animal models which are available—for example models developed in BALB/c mice—have not been tested for response to approved therapies for Graves' disease.

The present animal models for Graves' disease are therefore not optimal for studying potential therapies.

The present inventors have surprisingly found that an animal which is transgenic for human HLA-DR3 provides a suitable background for studying potential therapies. Thus in a further aspect the present invention provides an animal model for a disease associated with the production of TSHR antibodies, wherein the animal is transgenic for human HLA-DR3 and comprises increased levels of TSHR compared to a control animal.

The term "increased levels of TSHR" is intended to encompass an increased level of any of the full length TSHR sequence, for example TSHR peptides.

The level of TSHR is increased over a suitable control animal (e.g. an animal which is transgenic for human HLA-DR3 but which does not have increased TSHR). The level of TSHR may be increased by any suitable means. For example, by administering a vector comprising a nucleic acid which encodes a TSHR peptide. In a preferred embodiment the vector is a viral vector.

In a further embodiment, the invention provides a method for producing an animal model of a disease associated with the production of TSHR antibodies, said method comprising increasing the level of TSHR in an animal which is transgenic for human HLA-DR3.

In a preferred embodiment the method comprises increasing the level of TSHR by introducing a vector comprising a nucleic acid which encodes a TSHR peptide. In a more preferred embodiment the vector is a viral vector.

The animal model has features which are relevant to diseases associated with the production of TSHR antibodies. For example, in the animal model, levels of TSHR antibodies are increased compared to equivalent control animals in which levels of TSHR are not increased. The levels of TSHR antibodies may be increased at least 2-, 3-, 5-, 10-, 100- or 1000-fold compared to an equivalent control animal in which levels of TSHR antibodies are not increased.

The levels of TSHR antibodies may be determined using standard methods which are known in the art, for example an ELISA assay. The level of TSHR antibodies may be determined in a sample in vitro. For example, the sample may be a serum sample.

Transgenic for human HLA-DR3' means that the animal expresses the human MHC class II cell surface molecule HLA-DR3. The transgenic animal may be generated using suitable methods which are well known in the art.

'Associated with the production of TSHR antibodies' means that TSHR antibodies contribute to disease aetiology. For example, levels of TSHR antibodies may be increased in the disease compared to the levels in the absence of the disease. The disease associated with TSHR antibodies may be Graves' disease.

The TSHR may be human TSHR. For example, the TSHR may be the human TSHR A subunit or part thereof.

A nucleic acid encoding a TSHR may be provided using methods which are well known in the art, for example based on the TSHR sequence described herein.

The nucleic acid may be natural, synthetic or recombinant. It may be double or single stranded, it may be DNA or RNA or combinations thereof. It may, for example, be cDNA, a PCR product, genomic sequence or mRNA.

The nucleotide sequence may be codon optimised for production in the host/host cell of choice.

Delivery of the nucleotide sequence encoding TSHR may be mediated by viral infection. Suitable viral vectors are well known in the art. For example the viral vector may be an adenovirus, retrovirus or lentivirus.

In particular, the viral vector may be an adenovirus.

Production of the animal model may comprise multiple administrations of the vector.

The vector, for example adenovirus, may be administered at 3 week intervals, For example, the vector may be administered at an interval of 18-25, 18-23, 19-23 or 20-22 days. The vector may be administered at an interval of 20, 21 or 22 days.

The animal model may comprise administering the adenovirus vector on at least two occasions. For example the adenovirus vector may be administered on two or three occasions. In particular, the animal model may comprise administering the adenovirus vector on two occasions.

The animal model may comprise administering the vector on two occasions, with an interval of three weeks between administrations.

The vector, for example adenovirus, may be administered at a dose of $10^8$ to $10^{11}$ viral particles per administration. In particular, the adenovirus may be administered at a dose of $10^9$ to $10^{11}$ viral particles per administration. The adenovirus may be administered at a dose of $10^9$ viral particles per administration.

The vector may be administered by any suitable means. For example, in the case of an adenoviral vector, the vector may be administered by intramuscular injection.

The animal may be a mammal. For example the animal may be a mouse, rat, rabbit, guinea pig or primate. Preferably, the animal is a mouse.

In one embodiment the mouse is a HLA-DRA1*01:01 and HLA-DRB1*03:01 transgenic mouse on a mixed genetic background. Means for generating such a mouse will be known to one skilled in the art.

By way of example, the mouse model described in the Examples section was generated using the following approach: a 6-kb NdeI fragment of a HLA-DRA genomic clone in pUC and a 24-kb ClaI×SalI fragment of cos 4.1 containing the B gene were co-injected into fertilised eggs from (C57BL/6×DBA/2) F1 donors mated with C57BL/6 males. The offspring has later been bred into the IA-beta knockout C57BL/6 genetic background (AB0 mice) lacking mouse MHC class II molecule expression. These DR3tg mice express the HLA-DR3 molecule but not the mouse MHC-II molecule. This method is not exhaustive and alternative methods for generating HLA-DR3 transgenic mice, for example on a C57BL/10 background, are known in the art.

The invention will now be further described by way of Examples, which are meant to serve to assist one of ordinary skill in the art in carrying out the invention and are not intended in any way to limit the scope of the invention.

EXAMPLES

Example 1—ATX-GD-59 Induces TSHR-Specific T Cell Tolerance and Reduces Anti-TSHR Antibody Titers in Animal Models in HLA-DR3 Transgenic Mice Material, Methods and Procedures Mice DR3tg mice were bred under specific pathogen-free conditions externally at Charles River, UK or InnoSer, NL. The DR3tg strain was originally created by Strauβ et al. In brief, genomic constructs used were a 6 kb Nde I fragment of a HLA-DRA genomic clone in pUC 13 and a 24 kb CLa I×Sal I fragment of cos 4.1, a cosmid (pTCF) containing the B gene of DRB1*0301. A solution containing 1-2 µg/mL of each construct was used for co-injection into fertilized eggs from (C57Bl/6×DBA/2)F1 donors mated with C57Bl/6 males. The offspring were bred onto the IA-beta knockout C57BL/6 genetic background (AB$^0$ mice) lacking mouse MHC class II molecule expression. These DR3tg mice express the human MHC class II, HLA-DR3 molecule but not the mouse MHC class II molecule. Transgenic mice were identified by Southern blot analysis of tail DNA digested with Eco RI and probed with a 1.35 kb Bam HI fragment of the DRA cDNA and a 1.25 kb Bam HI fragment of the DRB1*0301 cDNA. DR3tg mice were used for these experiments as it has been suggested that this MHC class II molecule is associated with increased susceptibility to Graves' disease.

Animal studies were approved by the 'Ethical Committee for Animal experiments' at Hassett University and performed with the standards of care in a pathogen-free facility.

Antigens

Peptides were synthesized by PolyPeptide Laboratories (PPL; Strasbourg, France) and stored at a stock solution of 8 mg/ml in PBS at −20° C. The manufacturing process is based on solid phase peptide synthesis applying N-α-Fmoc protected amino acids as building blocks in the assembly of the peptide. The C-terminal residue is coupled to the MBHA resin as part of the Fmoc-lys(Boc)-MPPA-linker. The other amino acids are incorporated by a succession of Fmoc deprotection and amino acid coupling cycles. Figure legends indicate when PPL peptides have been used.

Alternatively, peptides were synthesized by GL Biochemistry Ltd (GLS; Shanghai, China) or by Severn Biotech Ltd (Severn, Kidderminster Worcs., UK) and stored at a stock solution of 20 mg/mL in DMSO (Sigma-Aldrich) at −80° C. The peptides were synthesized using F-moc chemistry with an N-terminal free amine and a C-terminal amide. Different peptide suppliers are indicated per experiment.

Peptides was used for treatment as single peptide (9B-N, 5D-K1) or as a peptide cocktail ATX-GD-59. ATX-GD-59 is an equimolar mix of 9B-N and 5D-K1 and indicated doses of ATX-GD-59 refers to the individual peptide content i.e. the total peptide amount administered is 2× the indicated treatment dose.

Human recombinant extracellular domain of TSHR (TSHR-ECD, AA19-417) was produced in *Trichoplusia ni* larval expression system using the Chesapeake PERL technology PERLXpress by Chesapeake PERL (Savage, USA). Protein quality of each lot TSHR-ECD was evaluated by SDS-PAGE gel and Western blot analysis.

Adenoviral vectors were purchased from Viraquest (North Liberty, Iowa, USA). Construction and purification of adenovirus containing TSHR amino acid residues 1-289 (Ad-TSHR) has been described previously. In brief, the adenoviral Ad-TSHR and control construct (Ad-LacZ) expressing β-galactosidase were propagated in HEK293 cells and purified by CsCL density gradient centrifugation. Viral particle concentration was determined by measuring the absorbance at 260 nm.

Ex Vivo Tolerization Experiment

DR3tg mice were injected subcutaneously in the flank region with 0.1 µg, 1 µg and 10 µg peptides on days −15, −13 and −11 respectively, followed by 3 injections of 100 µg (top dose/peptide) soluble peptide (5D-K1 or 9B-N) on days −8, −6 and −4 (dose escalation schedule). The ATX-GD-59 is an equimolar mix of the peptides 5D-K1 (SEQ ID NO:1) and 9B-N (SEQ ID NO:2) and the top dose mentioned (nmol) is per peptide in the cocktail. A peptide dose of 100 ug corresponds to ~45 nmol as both systems been used in different experiments. The peptides were administered subcutaneous in PBS. Alterations in top doses/peptide, and correspondingly in dose escalation doses, are indicated per experiment. On day 0, the mice were immunized subcutaneously in the base of the tail with 50 µg corresponding to the parental peptide (non-modified 5D and/or 9B) emulsified in Complete Freund adjuvants (CFA; 2 mg/ml *Mycobacterium tuberculosis* H37RA (Difco Laboratories, Michigan, US) in Incomplete Freund adjuvant (Difco)) (50 µg peptide in 100 µL CFA (100 µg H37RA)/injection). Ten days after immunization, draining LN and spleens were harvested. LN cells and splenocytes were isolated and cultured in X-vivo 15 medium supplemented with 2 mM L-glutamine, 50 U/mL penicillin and 50 U/mL streptomycin (all Lonza, Verviers, Belgium) in 96-well flat bottom plates. To investigate antigen-induced cell proliferation, 0.5×10$^6$ cells/well were cultured (200 µL/well) for 72 hours with TSHR-ECD in a concentration range of 0-25 µg/mL or with 12.5 µg/mL purified protein derivative (PPD; immunisation control; Statens serum institut, Copenhagen, Denmark). After 72 hours in a 37° C. incubator with 5% CO$_2$, 60 µL of cell supernatant was harvested and frozen. 20 µL/well of tritiated thymidine (PerkinElmer, Zaventem, Belgium) were then added to the cells to obtain a final concentration of 1 µCi/well. The cells were incubated at 37° C. and 5% CO$_2$, and after 16 h, plates were frozen. Thawed plates were harvested and read on a β-counter (Wallac 1450 Microbeta Trilux Liquid Scintillation Counter) to assess cell proliferation.

Adenoviral Animal Model for GD

DR3tg mice were injected subcutaneously in the flank region with 22.5 pmol, 225 pmol and 2250 pmol ATX-GD-59 or control treatment on days −15, −13 and −11 respectively, followed by 3 injections of 22.5 nmol ATX-GD-59 (top dose/peptide) or control treatment on days −8, −6 and −4 (dose escalation schedule). Alterations in top doses, and correspondingly in dose escalation doses, are indicated per experiment.

On day 0, mice were injected intramuscularly in the thigh muscle with Ad-TSHR or Ad-LacZ ($10^{10}$ viral particles). All mice were immunized simultaneously using the same batch of adenovirus per experiment. Mice were injected on two occasions at three weekly intervals (week 0 and 3) and blood was drawn at different time points according to the protocol shown in FIG. 2. Mice were euthanized 5 weeks after the first immunization to obtain blood, spleen cells and thyroid glands. Splenocytes were isolated and cultured in X-vivo 15 medium supplemented with 2 mM glutamine, 50 U/mL penicillin and 50 U/mL streptomycin (all Lonza, Verviers, Belgium) in 96-well flat bottom plates. To investigate antigen-induced cell proliferation, $0.5\times10^6$ cells/well were cultured (200 μl/well) for 72 hours with different concentrations of TSHR-ECD (0-25 μg/ml). After 72 hours in a 37° C. incubator with 5% $CO_2$, 60 μL of cell supernatant was harvested and frozen. 20 μL/well of tritiated thymidine (PerkinElmer, Zaventem, Belgium) were then added to the cells to obtain a final concentration of 1 μCi/well. The cells were incubated at 37° C., and after 16 h, plates were frozen. Thawed plates were harvested and read with β-counter (Wallac 1450 Microbeta Trilux Liquid Scintillation Counter) to assess the cell proliferation.

Detection of Anti-TSHR Antibodies

Anti-TSHR antibodies (IgG class) against purified recombinant TSHR-ECD (Chesapeake-Perl) were measured using ELISA. 96-well plates (half area 96-well, Fisher Scientific) were coated overnight at room temperature (RT) with 50 μl/well of TSHR-ECD protein in PBS (0.5 μg/ml). After washing with PBS-0.05% Tween20, wells were blocked with 1% BSA (w/v) in PBS for 1 h at RT and incubated with test sera (1:50 or 1:500 dilution). Mouse anti-TSHR antibody (A9, Abcam, Cambridge, UK) was used as a positive control. Antibody binding was then detected with horseradish peroxidase (HRP)-conjugated goat anti-mouse IgG (Abcam). To detect anti-TSHR antibodies of IgG1, IgG2a, IgG2b and IgG2c isotypes, HRP-conjugated rat anti-mouse IgG1 (Southern Biotech, Alabama, USA), goat anti-mouse IgG2a (Southern Biotech), gout anti-mouse IgG2b (Abcam) and goat anti-mouse IgG2c (Abcam) antibodies were used respectively. The signal was developed with tetramethylbenzidine (TMB). Optical density (OD) was measured in a plate reader at 450 nm (Tecan Benelux).

Detection of Stimulatory Anti-TSHR Antibodies (TSAbs)

Lulu* cells, Chinese Hamster Ovary-K1 (CHO-K1) cells stably transfected with pA3Luc, a cAMP responsive luciferase construct, and pcDNA3-TSHR, the human TSHR together with G418 resistance, were kindly provided by prof. M. Ludgate (Cardiff University, UK)[9]. Cells were maintained in Ham's 12 medium (Lonza) supplemented with 2 mM L-glutamine, 50 U/mL penicillin, 50 U/mL streptomycin (all Lonza), 10% foetal bovine serum (FBS) (Fisher Scientific, Aalst, Belgium) and 0.2 mg/mL geneticin (Fisher) at 37° C. in 5% $CO_2$. To measure TSAbs, cells were plated at $2*10^4$ cells/well in a 96-well plates in Ham's F12 medium with 10% charcoal stripped serum (Sigma-Aldrich, Bornem, Belgium). The next day, culture medium was removed and cells were incubated with fresh Ham's medium containing 5% PEG and 10% test serum for 4 h at 37° C. Then, cells were lysed with luciferase cell culture lysis buffer (Promega, Leiden, The Netherlands). The cAMP responsive luciferase production was measured by a luciferase reporter assay (Promega) according to the manufacturer's instructions and light emission was measured with a FLUOstar omega luminometer (BMG labtech, Ortenberg, Germany). Results are expressed as relative light units (RLU; light emission of stimulated cells/light emission of non-stimulated cells).

Detection of Hyperthyroidism

Total thyroxine (T4) was measured in undiluted mouse serum (10 μl) using the CBI mouse/rat thyroxine ELISA kit (Calbiotech, Spring Valley, Calif., USA) according to the manufacturer's instructions. T4 values were computed from standards in the kit and expressed as μg/dl.

Results

Single Peptide Treatment Induces TSHR-Specific T Cell Tolerance

Figure 1:
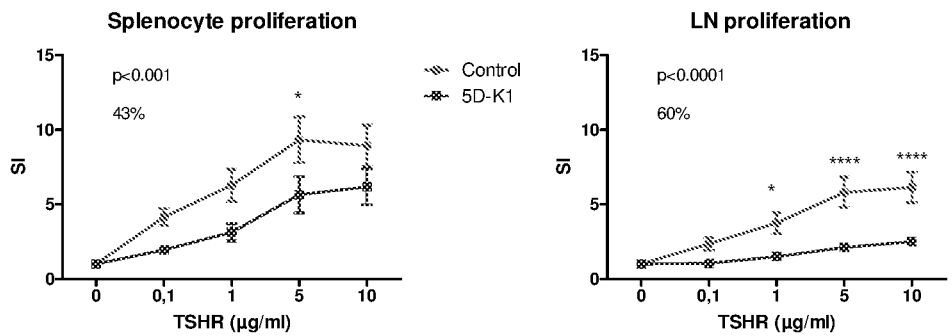
Figure 2:
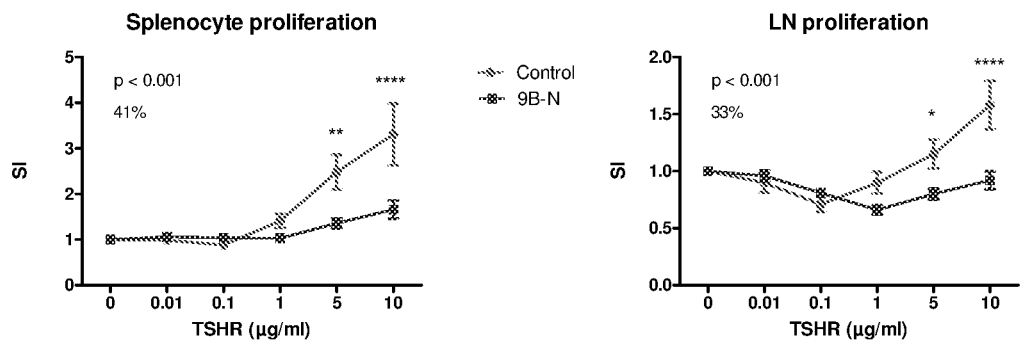

To determine the tolerogenic effect of single peptides 5D-K1 and 9B-N, HLA-DR transgenic mice were treated according to the dose escalation schedule first with one of the peptides alone. In the first experiment, DR3tg mice received a 5D-K1 or control-treatment, as described in the method section. Pretreatment with this modified apitope reduced TSHR-induced T cell proliferation by 43% in spleen samples and by 60% in LN samples when compared to control-treated animals (see FIGS. 1 and 2).

To investigate the tolerogenic capacity of peptide 9B-N, DR3tg mice were treated with 9B-N or PBS. This study showed that pretreatment with 9B-N significantly reduces the T cell proliferation towards the TSHR by 41 and 33% in spleen and LN samples, respectively.

Combined Peptide Treatment Induces TSHR-Specific T Cell Tolerance

The findings that a peptide treatment with individual peptides 5D-K1 or 9B-N reduces the TSHR-specific lymphocyte proliferation in mice led to the investigation whether a combined treatment, administrating the peptides as a cocktail, could reduce the TSHR-specific response as well. DR3tg mice were treated with ATX-GD-59 according to the dose escalation schedule and immunized with an emulsion including both parental, non-modified peptides in CFA. Three ATX-GD-59 top doses were tested (15; 22.5 and 45 nmol/peptide) for their potentially different tolerizing capacity, but no differences could be observed between the treatment doses (data not shown). Representative results are shown in FIG. 3 indicated that ATX-GD-59 treatment induced significant levels of TSHR-specific tolerance. TSHR-induced proliferation was reduced by 58% and 54% in splenocytes and LN cells, respectively.

Combined Peptide Treatment Reduces Anti-TSHR Antibody Production in the Adenoviral-Based Graves Disease Animal Model To demonstrate the therapeutic efficacy of ATX-GD-59, it was investigated whether the peptide treatment with ATX-GD-59 was able to suppress the presence of Graves disease parameters such as TSHR-specific splenocyte proliferation and the development of anti-TSHR antibodies. DR3tg mice received ATX-GD-59 or control treatment according to the dose escalation schedule followed by two immunizations with Ad-LacZ or Ad-TSHR viral particles. First, the effect of ATX-GD-59 treatment on TSHR-specific splenocyte proliferation was investigated. Splenocytes of Ad-LacZ immunized mice do not proliferate upon in vitro TSHR restimulation (data not shown). The TSHR-specific splenocyte absolute proliferation values in control-treated, Ad-TSHR immunized DR3tg mice are low but increase dose-dependently. As shown in FIG. 4, ATX-GD-59 treatment with 22.5 nmol top dose/peptide was able to significantly reduce the TSHR-specific splenocyte proliferation by more than 40%. ATX-GD-59 treatment with 15 nmol of each peptide showed similar results (data not shown). A similar tolerizing effect of ATX-GD-59 treatment was observed in a repeat experiment (data not shown), thereby confirming the reproducibility of these results.

Then, the effect of ATX-GD-59 treatment on anti-TSHR antibody development was investigated. Serum samples were collected to measure anti-THSR IgG levels via ELISA. No anti-TSHR IgG antibodies were present before (W-2, data not shown) and after (W0) ATX-GD-59 peptide pre-treatment (FIG. 5). Corresponding to the proliferation data, no anti-TSHR antibodies were detected in Ad-LacZ control immunized mice. High anti-TSHR IgG levels were observed in peptide control-treated mice at 2 weeks after the first Ad-TSHR immunization. ATX-GD-59 treatment reduced the increase in anti-TSHR antibodies seen in peptide control-treated mice upon Ad-TSHR immunization by 95% at week 2. Furthermore, the anti-TSHR IgG levels were still reduced by 93% at week 5 by the ATX-GD-59 peptide treatment.

To further investigate the reduction in anti-TSHR antibody levels, the effect of ATX-GD-59 treatment on different anti-TSHR isotype antibodies was investigated. Ad-TSHR immunization at $10^{10}$ viral particles induced high levels of anti-TSHR antibodies of isotype IgG2b and IgG2c. FIG. 6 shows that ATX-GD-59 significantly reduced anti-TSHR antibodies of the IgG1, IgG2b and IgG2c isotype in Ad-TSHR immunized mice, thereby correlating to the pattern of total IgG antibody levels shown in FIG. 5. Both 15 nmol and 22.5 nmol dose treatment regimes of ATX-GD-59 treatment were tested twice in two independent experiments and they significantly reduced anti-TSHR total IgG and IgG isotype levels (data of 15 nmol dose not shown), thereby indicating that both doses have efficacy in the adenoviral-based GD model.

Taken together, these results show that prophylactic ATX-GD-59 treatment is efficacious in inducing TSHR-specific T cell tolerance in the ex vivo tolerance model and in reducing anti-TSHR antibody levels in the adenoviral Graves' disease model.

Example 2—Co-Medication of ATX-GD-459 and Clinically Used Drugs for Graves' Disease Materials and Methods Mice DR3tg mice were bred under specific pathogen-free conditions externally at Charles River, UK. The DR3tg strain was originally created by Strauss et al (Strauss et al, 1994, Immunogenetics 3, 104-108). In brief, the genomic constructs used were a 6 kb NdeI fragment of a HLA-DRA genomic clone in pUC 13 and a 24 kb ClaIxSalI fragment of cos 4.1, a cosmid (pTCF) containing the B gene of DRB1*0301. A solution containing 1-2 µg/mL of each construct was used for co-injection into fertilised eggs from (C57BL/6xDBA/2) F1 donors mated with C57BL/6 males. The offspring has later been bred into the IA-beta knockout C57BL/6 genetic background (AB0 mice) lacking mouse MHC class II molecule expression. These DR3tg mice express the HLA-DRB1*0301 molecule but not the mouse MHC-II molecule. The mice were maintained by backcrossing to C57BL/6 and to B10.Q. Transgenic mice were identified by Southern blot analysis of tail DNA digested with EcoRI and probed with a 1.35 kb BamHI fragment of the DRA cDNA and a 1.25 kb BamHI fragment of the DRB1*0301 cDNA. DR3tg mice were used for these experiments as it has been suggested that this MHC class II molecule is associated with an increased risk for individuals to develop Graves' disease.

The DR4 mouse strain was originally created by Lars Fugger et al (PNAS 1994 volume 91: 6151-55) in that a HLA-DRA*0101/HLA-DRB1*0401 and mCD3-huCD4c/g constructs were co-microinjected into embryos from (DBA/1×A/CA) F1 matings and viable embryos were transferred into pseudopregnant female (BALB/c×129) F1 for development to term. The offspring has later been bred into the IA-b knockout genetic background (AB0 mice) lacking mouse MHC class II molecule expression. The only MHC class II molecule expressed in these DR4 mice is therefore the human HLA DR4 molecule.

BALB/cJOlaHsd mice were obtained from Harlan Laboratories (Venray, The Netherlands).

Animal studies were approved by the 'Ethical Committee for Animal experiments' (ECD) at Hassett University and performed in a pathogen-free facility.

Antigens

All single peptides were synthesized by GL Biochem Ltd (Shanghai, China) and stored at a stock solution of 20 mg/ml in DMSO (Sigma-Aldrich) at −80° C. The peptides were synthesized with an N-terminal free amine and a C-terminal amide.

ATX-GD-459 peptides (see Example 3 for a discussion of these peptides) were synthesized by PolyPeptide Laboratories (Strasbourg, France) and stored at a stock solution of 8 mg/ml in PBS at −20° C. The manufacturing process is based on solid phase peptide synthesis applying N-α-Fmoc protected amino acids as building blocks in the assembly of the peptide. The C-terminal residue is coupled to the MBHA resin as part of the Fmoc-lys(Boc)-MPPA-linker. The other amino acids are incorporated by a succession of Fmoc deprotection and amino acid coupling cycles.

Human recombinant extracellular domain of TSHR (TSHR-ECD, AA19-417) was produced in a *Trichoplusia ni* larval expression system using the Chesapeake PERL technology PERLXpress by Chesapeake PERL (Savage, USA). Protein quality of each TSHR-ECD lot was evaluated by SDS-PAGE gel and Western blot analysis.

Adenoviral vectors were purchased from Viraquest (North Liberty, Iowa, USA). Construction and purification of adenovirus containing TSHR amino acid residues 1-289 (Ad-TSHR) has been described previously (Chen et al. 1999 J Clin Endocrinol Metab 84:3182-3186). In brief, adenoviruses Ad-TSHR and control adenovirus (Ad-LacZ) expressing β-galactosidase were propagated in HEK293 cells and purified by CsCL density gradient centrifugation. Viral particle concentration was determined by measuring the absorbance at 260 nm.

ATX-GD-459 and Clinically Used GD Drug Co-Medication in an Adenoviral-Based Animal Model for GD DR3tg mice (n=9-10/group) were injected subcutaneously in the flank region with 15 pmol, 150 pmol and 1500 pmol of each ATX-GD-459 peptide or control peptide on days −15, −13 and −11 respectively, followed by 3 injections of 15 nmol of each ATX-GD-459 peptide (top dose) or control peptide on days −8, −6 and −4 (dose escalation schedule). Alterations in top doses, and correspondingly in dose escalation doses, are indicated per experiment. Starting on the day of the first peptide treatment until termination of the experiment, mice were treated either MMI or propranolol. MMI (Sigma-Aldrich, Bornem, Belgium) was dissolved in sterile water at the desired concentration to give mice a daily dose of 500 µg via subcutaneous administration by ALZET osmotic pumps (model 1004, 0.11 µL/h; Charles River, France). New osmotic pumps were implanted after 4 weeks. Propranolol hydrochloride (Sigma-Aldrich) was dissolved freshly in 0.9% saline and administered via daily intraperitoneal (IP) injections at a dose of 10 mg/kg/day. On day 0, mice were immunized by intramuscular injection with $10^9$ or $10^{10}$ Ad-TSHR viral particles and the immunization was repeated three weeks later. Body weight was recorded on a weekly base to measure the health status of the mice. Mice were euthanized 5 weeks after the first immunization to obtain blood, thyroid and spleen samples. TSHR-induced splenocyte proliferation, cytokine secretion and anti-TSHR antibody levels were assessed as described below.

Detection of Anti-TSHR Antibodies

Anti-TSHR antibodies (IgG class) against purified recombinant TSHR-ECD (Chesapeake-Perl) were measured using ELISA. 96-well plates (half area 96-well, Fisher Scientific) were coated overnight at room temperature (RT) with 50 μl/well of TSHR-ECD protein in PBS (0.5 μg/ml). After washing with PBS-0.05% Tween20, wells were blocked with 1% BSA (w/v) in PBS for 1 h at RT and incubated with test sera (1:50 or 1:500 dilution). Mouse anti-TSHR antibody (A9, Abcam, Cambridge, UK) was used as a positive control. Antibody binding was then detected with horseradish peroxidase (HRP)-conjugated goat anti-mouse IgG (Abcam). To detect anti-TSHR antibodies of IgG1, IgG2a, IgG2b and IgG2c isotypes, HRP-conjugated rat anti-mouse IgG1 (Southern Biotech, Alabama, USA), goat anti-mouse IgG2a (Southern Biotech), goat anti-mouse IgG2b (Abcam) and goat anti-mouse IgG2c (Abcam) antibodies were used respectively. The signal was developed with tetramethylbenzidine. Optical density (OD) was measured in a plate reader at 450 nm (Tecan Benelux).

Detection of Stimulatory Anti-TSHR Antibodies (TSAbs)

Lulu* cells, Chinese Hamster Ovary-K1 (CHO-K1) cells stably transfected with pA3Luc, a cAMP responsive luciferase construct, and pcDNA3-TSHR, the human TSHR together with G418 resistance, were kindly provided by prof. M. Ludgate (Cardiff University, UK)6. Cells were maintained in Ham's 12 medium (Lonza) supplemented with 2 mM L-glutamine, 50 U/mL penicillin, 50 U/mL streptomycin (all Lonza), 10% foetal bovine serum (FBS) (Fisher Scientific, Aalst, Belgium) and 0.2 mg/mL geneticin (Fisher) at 37° C. in 5% CO2. To measure TSAbs, cells were plated at $2*10^4$ cells/well in a 96-wells plates in Ham's F12 medium with 10% charcoal stripped serum (Sigma-Aldrich, Bornem, Belgium). The next day, culture medium was removed and cells were incubated with fresh Ham's medium containing 5% PEG and 10% test serum for 4 h at 37° C. Then, cells were lysed with luciferase cell culture lysis buffer (Promega, Leiden, The Netherlands). The cAMP responsive luciferase production was measured by a luciferase reporter assay (Promega) according to the manufacturer's instructions and light emission was measured with a FLUOstar omega luminometer (BMG labtech, Ortenberg, Germany). Results are expressed as relative light units (RLU; light emission of stimulated cells/light emission of non-stimulated cells).

Detection of Hyperthyroidism

Total thyroxine (T4) was measured in undiluted mouse serum (10 μl) using the CBI mouse/rat thyroxine ELISA kit (Calbiotech, Spring Valley, Calif., USA) according to the manufacturer's instructions. T4 values were computed from standards in the kit and expressed as μg/dl.

Splenocyte Proliferation Assay

Splenocytes were isolated and cultured in X-vivo 15 medium supplemented with 2 mM glutamine, 50 U/mL penicillin and 50 U/mL streptomycin (all Lonza, Verviers, Belgium) in 96-well flat bottom plates. To investigate antigen-induced cell proliferation, $0.5 \times 10^6$ cells/well were cultured (200 μl/well) for 72 hours with different concentrations of TSHR-ECD (0-25 μg/ml). After 72 hours in a 37° C. incubator with 5% CO2, 60 μL of cell supernatant was harvested and frozen. 20 μL/well of tritiated thymidine (PerkinElmer, Zaventem, Belgium) were then added to the cells to obtain a final concentration of 1 μCi/well. The cells were incubated at 37° C., and after 16 h, plates were frozen. Thawed plates were harvested and read with a β-counter (Wallac 1450 Microbeta Trilux Liquid Scintillation Counter) to assess the cell proliferation.

Results

Co-Medication of MMI and ATX-GD-459 in Adenoviral-Based GD Model

To verify whether ATX-GD-459 treatment can be combined with MMI to treat GD symptoms, the effect of MMI and ATX-GD-459 co-medication was investigated in the adenoviral-based GD animal model (see Examples 4 and 5 for further discussion of the model). In this experiment, DR3tg mice were treated with the following combinations of MMI and ATX-GD-459: vehicle+control peptide, MMI+ control peptide, vehicle+ATX-GD-459 or MMI+ATXGD-459. Treatment with ATX-GD-459 or control peptide was administered during the first two weeks of the experiment according to the dose escalation schedule (FIG. 8). Subcutaneous vehicle or MMI treatment started simultaneously but lasted until termination of the experiment. This experimental design allowed the investigation of reciprocal influences of MMI and ATX-GD-459 treatments on GD-like disease parameters.

First, the effect of MMI and ATX-GD-459 treatment on TSHR-specific splenocyte proliferation was investigated. Absolute TSHR-specific splenocyte proliferation values were relatively low in the control-treated mice (FIG. 10). However, these values were much higher in this experiment than in all other control groups of previously performed experiments (data not shown) or of the propranolol experiment. Therefore, the significant reduction in TSHR-specific splenocyte proliferation caused by MMI or ATX-GD-459 treatment, as depicted in FIG. 10, should be interpreted with caution.

Next to the TSHR-induced splenocyte proliferation, anti-TSHR IgG serum levels were measured in all mice. Before onset of the experiment, no anti-TSHR IgG antibodies were detected in any of the mice (data not shown). A dose escalation treatment of ATX-GD-459 did not induce any production of anti-TSHR antibodies, as measured at week 0 (FIG. 11). Ad-TSHR immunization evoked the production of anti-TSHR antibodies in control peptide treated mice, but not in ATX-GD-459 treated mice. Although not significantly different due to substantial variation between control-treated mice, ATX-GD-459 pre-treatment reduced the average anti-TSHR antibody production by more than 90%. In contrast, MMI treatment had no effect on anti-TSHR antibody levels. In addition, MMI treatment did not influence the antibody reducing capability of ATX-GD-459 peptide treatment.

The anti-TSHR antibody profile was further investigated by determining the specific IgG isotypes. As shown in FIG. 12, none of the Ad-TSHR immunized mice produce anti-TSHR antibodies of the IgG1 isotype. Ad-TSHR immunization induced the production of anti-TSHR IgG2b and IgG2c antibodies in control peptide treated mice, but not in ATX-GD-459 treated mice. ATX-GD-459 pre-treatment reduced the production of both anti-TSHR IgG2b and IgG2c antibodies by more than 90%. In contrast, MMI treatment had no effect on any of the anti-TSHR IgG isotypes and did not affect the antibody reducing capability of ATX-GD-459 treatment. These data fully correspond to the profile observed for the anti-TSHR total IgG antibodies.

In addition to the isotype determination, the biologic activity of the anti-TSHR antibodies and the potential effect of MMI or ATX-GD-459 thereon were investigated. Since the threshold for stimulatory antibodies was not exceeded by any of the Ad-TSHR immunized mice (data not shown), no conclusions were drawn on the effect of MMI or ATX-GD-459 treatment on the incidence of stimulatory antibodies. The low incidence of stimulatory antibodies is in accordance with previously described experiments (report ATX-GD-15-003).

Finally, the effect of MMI and ATX-GD-459 treatment on T4 levels was examined. As no Ad-LacZ immunization was used as an immunization control in this experiment, the incidence of hyperthyroidism could not be determined. Although no information on the level of hyperthyroidism is available, the results clearly showed that MMI treatment significantly reduced T4 levels (FIG. 13). ATX-GD-459 pre-treatment, however, had no effect on serum T4 levels. In addition, ATX-GD-459 pretreatment had no influence on the T4-reducing capability of MMI.

Taken together, these data show that MMI and ATX-GD-459 treatment do not hamper each other's function and can be safely combined in the adenoviral-based GD model.

Co-Medication of Propranolol and ATX-GD-459 in Adenoviral-Based GD Model

GD patients often use β-blockers to fight the adrenergic symptoms of the hyperthyroidism.

Therefore, the effect of co-medication with ATX-GD-459 and β-blocker propranolol in the adenoviral-based GD model was investigated in this experiment. First, the TSHR-specific splenocyte proliferation was examined. As shown in FIG. 14, neither propranolol nor ATX-GD-459 treatment induced a significant effect on TSHR-specific splenocyte proliferation. A combined treatment of propranolol and ATX-GD-459 also had no effect on the proliferative response.

Then, the effect of propranolol and ATX-GD-459 treatment on anti-TSHR antibody development was investigated. Serum samples were collected to measure anti-THSR IgG levels via ELISA. No anti-TSHR IgG antibodies were present before (W-2) and after (W0) ATX-GD-459 peptide pretreatment (FIG. 15). Ad-TSHR immunization induced a strong production of anti-TSHR antibodies in control peptide treated mice, but to a lesser extent in ATX-GD-459 treated mice. Remarkably, the Ad-TSHR immunization using $10^{10}$ viral particles used in this experiment caused higher anti-TSHR antibody titers than $10^9$ Ad-TSHR immunization used in previous experiments (data not shown). ATX-GD-459 treatment reduced anti-TSHR antibody production by more than 90%, both when measured at W2 and W5 after immunization. In contrast, propranolol treatment had no effect on anti-TSHR antibody levels. In addition, propranolol treatment did not influence the antibody reducing capability of ATX-GD-459 peptide treatment.

Anti-TSHR IgG isotype profiles were then determined to further investigate the antibody profile. Although lower than IgG2b and IgG2c levels, anti-TSHR IgG1 antibodies were clearly induced by Ad TSHR immunization. These data are in contrast to the absence of anti-TSHR IgG1 antibodies in previous experiments (data not shown), but can be explained by the increase in adenoviral particle dose from $10^9$ to $10^{10}$ used at immunization. As shown in FIG. 16, ATX-GD-459 treatment significantly reduced anti-TSHR IgG2b and IgG2c antibody levels. Anti-TSHR IgG1 antibody titers were also reduced by peptide treatment, but not at a significant level. In contrast to the peptide treatment, propranolol treatment had no effect on any of the anti-TSHR IgG isotypes. In addition, propranolol treatment did not affect the antibody reducing capability of ATX-GD-459 treatment, thereby fully corresponding to the profile observed for the anti-TSHR total IgG antibodies.

Taken together, ATX-GD-459 treatment significantly reduced anti-TSHR antibody titers in this animal model. However, no effect of propranolol treatment on any GD-like disease parameter was observed. To verify whether daily IP administration induced pharmacological levels of propranolol in mouse blood, propranolol levels in mouse plasma were measured by LC-MSMS (Anacura). Blood samples were collected between 60 and 90 minutes post-dose and individual plasma levels compared between W0 and W5. The results are shown in FIG. 18.

Example 3—Ex Vivo T Cell Tolerisation with ATX-GD-459

Hybridoma clones specific for RNB-4K and RNB-5D were chosen to determine whether the RNB-4K-GKK and RNB-5D-K1 peptides were apitopes. 'Antigen processing independent presentation' (APIPS) assays were performed and RNB-4K-GKK and RNB-5D-K1 peptides were confirmed to be apitopes (FIG. 27).

The ability of a composition comprising the peptides shown in Table 1 (termed ATX-GD-459), or the individual peptides administered alone, to induce tolerance towards TSHR was determined. The ex vivo tolerisation protocol is shown in FIG. 19.

TABLE 1

| Peptide | Sequence | SEQ ID NO: |
|---|---|---|
| RNB-5D-K1 | KKKKYVSIDVTLQQLESHKKK | SEQ ID NO: 1 |
| RNB-4K-GKK | KKGNLPNISRIYVSIDVTGKK | SEQ ID NO: 4 |
| RNB-9B | GLKMFPDLTKVYSTD | SEQ ID NO: 2 |

HLA-DR3 mice were treated with ATX-GD-459 according to the dose escalation schedule and immunised with parental peptides 4K/5D/9B together in CFA. The results showed that ATX-GD-459 treatment induced significant levels of TSHR-specific tolerance in both spleen and LN cells (FIG. 20). The tolerance induced by the ATX-GD-459 treatment was greater than that induced by the administration of the individual peptides (FIG. 20).

Example 4—Establishment of an Adenoviral Based Graves' Disease Model

To validate the therapeutic effect of ATX-GD-459 peptide treatment, an adenoviral-based animal model was first established in wild-type BALB/c mice. TSHR-induced splenocyte proliferation, anti-TSHR IgG antibodies, serum levels of T4 and pathological changes in thyroid tissue were investigated as parameters for disease symptoms. In the first experiment, BALB/c mice were immunised with $10^8$ Ad-TSHR viral particles. Although this viral dose was described to induce hyperthyroidism and anti-TSHR antibody production (Chen et al, 2004, Endocrinology 145 (11): 4927-33), only 2/10 mice were considered (borderline) hyperthyroid and none of the mice produced anti-TSHR IgG antibodies (data not shown).

During a second experiment using an increased viral particle dose, around 30% of Ad-TSHR immunised mice had elevated serum T4 levels measured 4 weeks after the first immunisation (FIG. 22). However, an incidence rate of only 15% was observed at week 10. This decline in elevated T4 levels in wild-type BALB/c mice over time following an initial rise in the weeks post immunisation has been described before (McLachlan et al, 2012, Thyroid 8:1-7). Nevertheless, pronounced hyperthyroidism in individual mice corresponded well with histopathology findings in thyroid tissue such as hypertrophy of thyroid epithelial cells or lymphocyte infiltration (data not shown).

Although the literature provides evidence that mice with a C57BL/6 genetic background or DR3tg mice remain resistant to the development of Graves' disease-like symptoms, the inventors tested the ability of Ad-TSHR immunisation to induce Graves' disease-like symptoms in DR3tg mice with a mixed C57BL/10, DBA/2, C57BL/6 non-MHC class II genetic background.

FIG. 23A shows the serum T4 levels in Ad-LacZ and Ad-TSHR immunised DR3tg mice. Although 4 Ad-TSHR immunised mice showed T4 levels higher than the mean+ 2SD of the Ad-LacZ immunised mice, they were only borderline hyperthyroid and the increase in T4 levels was considered too low to use as a disease parameter when studying the efficacy of peptide treatment efficacy.

Ad-TSHR immunisation induced high anti-TSHR IgG titres in sera of DR3tg mice (FIG. 11, right panel). Highest anti-TSHR IgG levels are reached at 4 weeks followed by a decline in antibody levels at week 7 and 10, which is in contrast to the stable anti-TSHR IgG levels observed in BALB/c mice (FIG. 23C, left panel). The finding that anti-TSHR IgG levels in DR3tg mice are even higher at 2 weeks after the first immunisation than at 4 weeks (data not shown), led to the conclusion to terminate the adenoviral Graves' disease model at 4 instead of at 10 weeks.

Example 5—Validation of the Adenoviral Graves' Disease Model

To validate the DR3tg adenoviral Graves' disease model, the effect of different immune-modulating drugs on anti-TSHR antibody production in the adenoviral Graves' disease model was investigated. The anti-thyroid drug methimazole (MMI) is currently used to directly reduce thyroid hormone levels in Graves' disease patients. Therefore, the effects of MMI treatment in Ad-TSHR immunised DR3tg mice was determined. Two different MMI doses (50-500 μg/mouse/day) were tested, based on literature describing the hypothyroidism inducing effect of MMI in mice (Jeong et al, 2012, Endocrinology 153: 683-9; Mozes et al, 1998, J. Clin Immunology 18 (2): 106-13). A daily dose of 500 μg MMI significantly reduced T4 levels both at 2 and 4 weeks after the first immunisation, whereas the 50 μg dose only showed a trend towards reduced T4 levels (FIG. 24A). Although Ad-TSHR immunisation induced no hyperthyroidism in this (data of Ad-LacZ immunised mice not shown) and previous experiments, the reduction in T4 levels induced by MMI treatment indicates that the hormone production by thyroids of DR3tg mice can be affected.

In addition to its anti-thyroid function, MMI also exerts immune-modulatory effects (Mozes et al, 1998, as above; Wang et al, 2003, J. Leukoc. Biol. 73: 57-64). Therefore, it was determined whether MMI treatment can reduce anti-TSHR IgG production in Ad-TSHR immunised mice. Although MMI treatment significantly decreased T4 levels, no changes in anti-TSHR IgG levels were observed (FIG. 24B).

Graves' disease patients, in particular GO patients, often require immunosuppressive treatment with glucocorticoids. The effect of methylprednisolone, a synthetic glucocorticoid drug, on anti-TSHR antibody production in Ad-TSHR immunised mice was tested. A treatment of 7 mg/kg/day Methylprednisolone significantly reduced anti-TSHR IgG levels in Ad-TSHR immunised DR4tg mice, whereas a dose of 1 mg/kg/day was not sufficient to reduce the antibody titers (data not shown). A 7 mg/kg/day Methylprednisolone treatment of Ad-immunised DR3tg mice significantly reduced anti-TSHR IgG levels when measured at 2 weeks after the first immunisation, but not at 4 weeks, due to the natural decline of anti-TSHR antibody levels in non-treated mice with time. Methylprednisolone treatment also reduced thymic and spleen cell numbers, indicating sufficient pharmacological dose level in the adenoviral Graves' disease model (FIG. 25).

These data demonstrate the efficacy of apitopes in diseased DR3tg mice may be determined by measuring a reduction in anti-TSHR IgG antibodies.

Example 6—Demonstration of the Therapeutic Efficacy of ATX-GD-459 in Adenoviral Graves' Disease Model To determine whether the RNB-4K-GKK, RNB-5D-K1 and RNB-9B peptide combination (ATX-GD-459) was able to suppress the development of anti-TSHR antibodies, DR3tg mice received ATX-GD-459 or control treatment according to the dose escalation schedule followed by Ad-LacZ or Ad-TSHR immunisation. Serum samples were collected to measure anti-THSR IgG levels via ELISA. No anti-TSHR IgG antibodies were present before (W-2, data not shown) and after (W0) ATX-GD-459 peptide treatment (FIG. 25). High anti-TSHR IgG levels are observed in PBS-treated mice at 2 weeks after the first Ad-TSHR immunisation. ATX-GD-459 treatment reduced the increase in anti-TSHR IgG antibodies upon Ad-TSHR immunisation by 72% and 65% at week 2 and 5, respectively. These results show that ATX-GD-459 is efficacious in this adenoviral Graves' disease model.

High anti-TSHR IgG levels were observed upon Ad-TSHR immunisation. Therefore, this disease parameter was used to investigate the effect of immune-modulatory drugs or ATX-GD-459 peptide treatment in the adenoviral Graves' disease model. It was shown that methylprednisolone treatment successfully reduced anti-TSHR IgG levels in Ad-TSHR immunised DR3tg mice. Moreover, ATX-GD-459 peptide treatment according to the dose escalation schedule reduced the increase in anti-TSHR IgG antibody formation by 70%.

Materials & Methods

Mice

Mice were as described in Example 2.

Antigens

Antigens were as described in Example 2.

Antigen Processing Independent Presentation System (APIPS) Assay

Antigen-specific T cell hybridomas were tested for their reactivity to the peptides, presented by fixed or not fixed VAVY or BM14 cells (=APCs). $5 \times 10^4$ cells from the individual clones were cultured with 25 μg/ml peptide and $5 \times 10^4$ fixed or fresh APCs. To fixate APCs, cells were incubated with 0.5% paraformaldehyde (Merck, Darmstadt, Germany) (pH7) for 5 min at room temperature (RT). The fixation reaction was stopped by adding 0.4M glycine (Sigma-Aldrich) and washing the cells in RPMI-10% FCS. Additionally, reactivity towards human TSHR-ECD protein (Chesapeake-PERL, Savage, Md., USA) was measured to identify epitopes. After 48 h, antigen-induced IL-2 production was measured by ELISA.

Ex Vivo Tolerisation Experiment

DR3tg or DR4tg mice were injected subcutaneously in the flank region with 0.1 µg, 1 µg and 10 µg of peptide on days −15, −13 and −11 respectively, followed by 3 injections of 33, 75 or 100 µg peptide (depending on top dose, see Figure legends) on days −8, −6 and −4 (dose escalation schedule). Alterations in top doses, and correspondingly in dose escalation doses, are indicated per experiment. On day 0, the mice were immunised subcutaneously in the base of the tail with 50 µg antigen (non-modified parental 15-mer peptide) emulsified in CFA (peptide/CFA). Ten days after immunisation, draining lymph nodes (LN) and spleens were harvested. LN cells and splenocytes were isolated and cultured in X-vivo 15 medium (supplemented with 2 mM L-glutamine, 50 U/mL penicillin and 50 U/mL streptomycin; Lonza) in 96-well flat bottom plates. To investigate antigen-induced cell proliferation, $0.5\times10^6$ cells/well were cultured (200 µl/well) for 72 hours with different antigen concentrations (0-25 µg/ml) or with 12.5 µg/ml purified protein derivative (PPD; priming control; Statens serum institut, Copenhagen, Denmark). After 72 hours, 60 µL of cell supernatant was harvested and frozen. 20 µL/well of tritiated thymidine (PerkinElmer, Zaventem, Belgium) were then added to the cells to obtain a final concentration of 1 µCi/well. The cells were incubated at 37° C., and after 16 h, plates were frozen. Thawed plates were harvested and read with β-counter (Wallac 1450 Microbeta Trilux Liquid Scintillation Counter) to assess the cell proliferation.

Adenoviral Animal Model for Graves' Disease

Adenovirus expressing the human TSHR A-subunit (amino acid residues 1-289; Ad-TSHR) and control adenovirus (Ad-LacZ) expressing β-galactosidase were purchased from Viraquest (North Liberty, Iowa, USA). Six-week old female BALB/cJOlaHsd mice (Harlan Laboratories, Venray, The Netherlands) or DR3tg mice were injected intramuscularly in the thigh muscle with Ad-TSHR or Ad-LacZ ($10^9$, $10^{10}$ or $10^{11}$ viral particles). All mice were immunised simultaneously using the same batch of adenovirus per experiment. Mice were injected on two or three occasions at three weekly intervals (week 0, 3 and 6) and blood was drawn before the first immunisation and one week after the second immunisation. Mice were euthanized 4, 5 or 10 weeks after the first immunisation to obtain blood, spleen cells and thyroid glands. Splenocytes were isolated and cultured in X-vivo 15 medium (supplemented with glutamine, penicillin and streptomycin; Lonza) in 96-well flat bottom plates. To investigate antigen-induced cell proliferation, $0.5\times10^6$ cells/well were cultured (200 µl/well) for 72 hours with different antigen concentrations (0-25 µg/ml). After 72 hours, 60 µL of cell supernatant was harvested and frozen. 20 µL/well of tritiated thymidine (PerkinElmer, Zaventem, Belgium) were then added to the cells to obtain a final concentration of 1 µCi/well. The cells were incubated at 37° C., and after 16 h, plates were frozen. Thawed plates were harvested and read with β-counter (Wallac 1450 Microbeta Trilux Liquid Scintillation Counter) to assess the cell proliferation.

Detection of Anti-TSHR Antibodies

Anti-TSHR antibodies (IgG class) against purified TSHR-ECD protein (Chesapeake-Perl) were measured using ELISA. 96-well plates (half area 96-well, Fisher Scientific) were coated overnight at RT with 50 µl/well of TSHR-ECD protein in PBS (0.5 µg/ml). After washing with PBS-0.05% Tween, wells were blocked with 1% Bovine Serum Albumin (BSA) (w/v) in PBS for 1 h at RT and incubated with test sera (duplicate aliquots, 1:50 dilution). Mouse anti-TSHR antibody (A9, Abcam, Cambridge, UK) was used as a positive control. Antibody binding was then detected with horseradish peroxidase (HRP)-conjugated goat anti-mouse IgG (Abcam). To detect anti-TSHR antibodies of IgG1, IgG2a, IgG2b and IgG2c isotypes, HRP-conjugated rat anti-mouse IgG1 (Southern Biotech, Alabama, USA), goat anti-mouse IgG2a (Southern Biotech), goat anti-mouse IgG2b (Abcam) and goat anti-mouse IgG2c (Abcam) antibodies were used respectively. The signal was developed with tetramethylbenzidine (TMB). Optical density (OD) was measured in a plate reader at 450 nm (Tecan Benelux).

Detection of Stimulatory Anti-TSHR Antibodies (TSAbs)

Lulu* cells, Chinese Hamster Ovary-K1 (CHO-K1) cells stably transfected with pA3Luc, a cAMP responsive luciferase construct, and pcDNA3-TSHR, the human TSHR together with G418 resistance, were kindly provided by Prof. M. Ludgate (Cardiff University, UK). Cells were maintained in Ham's 12 medium (Lonza, Verviers, Belgium) with 2 mM L-glutamine (Lonza), 50 U/mL penicillin and 50 U/mL streptomycin (Lonza), 10% foetal bovine serum (FBS) (Fisher Scientific, Aalst, Belgium) and 0.2 mg/mL geneticin (Fisher) at 37° C. in 5% CO2. To measure TSAbs, cells were plated at $2*10^4$ cells/well in a 96-wells plates in Ham's F12 medium with 10% charcoal stripped serum (Sigma-Aldrich, Bornem, Belgium). The next day, culture medium was removed and cells were incubated with fresh Ham's medium containing 5% PEG and 10% test serum for 4 h at 37° C. Then, cells were lysed with luciferase cell culture lysis buffer (Promega, Leiden, The Netherlands). The cAMP responsive luciferase production was measured by a luciferase reporter assay (Promega) according to the manufacturer's instructions and light emission was measured with a FLUOstar omega luminometer (BMG labtech, Ortenberg, Germany). Results are expressed as relative light units (RLU; light emission of stimulated cells/light emission of non-stimulated cells).

Detection of Hyperthyroidism

Total thyroxine (T4) was measured in undiluted mouse serum (10 µl) using the CBI mouse/rat thyroxine ELISA kit (Calbiotech, Spring Valley, Calif., USA) according to the manufacturer's instructions. T4 values were computed from standards in the kit and expressed as µg/dl. In addition to serum T4 determinations, thyroid histology was used as a parameter for hyperthyroidism. Thyroid glands were fixed in 10% neutral buffered formalin (pH 7.5), processed to sections and stained with hematoxylin and eosin. Sections were observed for pathological changes (hypertrophy, hypercellularity of epithelial cells and infiltration of lymphocytes) and scored (KWS Biotest, Bristol, UK).

Validation of the Graves' Disease Animal Model

DR3tg mice were intramuscularly immunised with Ad-TSHR on two occasions on a three weekly interval (day 0 and 21). Starting on the day of the first immunisation until termination of the experiment, mice were treated with either MMI or 6α-methylprednisolone 21 hemisuccinate sodium salt (Methylprednisolone). All compounds were administered subcutaneously by ALZET osmotic pumps (model 1004, 0.11 µL/h, Charles River, France). MMI (Sigma) was dissolved in sterile water at the desired concentration to give the mice a daily dose of 50 or 500 µg. Methylprednisolone (Sigma) was dissolved in sterile water and administered to the mice at a dose of 1 mg/kg/day or 7 mg/kg/day. Body weight was recorded on a weekly base to measure the health status of the mice. Mice were euthanized 4 weeks after the first immunisation to obtain blood and spleen samples.

TSHR-specific splenocyte proliferation and anti-TSHR antibody levels were assessed as described above.

Prophylactic Graves' Disease Animal Model

DR3tg mice were injected subcutaneously in the flank region with 0.1 μg, 1 μg and 10 μg ATX-GD-459 or control treatment on days −15, −13 and −11 respectively, followed by 3 injections of 100 μg ATX-GD-459 (top dose) or control treatment on days −8, −6 and −4 (dose escalation schedule). Alterations in top doses, and correspondingly in dose escalation doses, are indicated per experiment. On day 0, mice were immunised by intramuscular injection with $10^9$ Ad-TSHR or Ad-LacZ viral particles and the immunisation was repeated three weeks later. Five weeks after the first immunisation, blood and spleens were collected. TSHR-specific splenocyte proliferation and anti-TSHR antibody levels were assessed as described above.

Various modifications and variations of the described invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or biology or related fields are intended to be covered by the present invention. All publications mentioned in the above specification are herein incorporated by reference.

---

The invention claimed is:

1. A composition which comprises the following peptides:
   (i) a peptide comprising the amino acid sequence KKK-KYVSIDVTLQQLESHKKK (SEQ ID NO: 1), or a sequence having at least 85% sequence identity to SEQ ID NO: 1; and
   (ii) a peptide comprising the amino acid sequence GLK-MFPDLTKVYSTD (SEQ ID NO: 2), or a sequence having at least 85% sequence identity to SEQ ID NO: 2.

2. The composition according to claim 1, further comprising an antithyroid agent and/or a β-blocker.

3. A method for suppressing the production of thyroid stimulating hormone receptor (TSHR) autoantibodies in a subject, comprising a step of administering the composition according to claim 1 to the subject.

4. A method for treating Graves' Disease in a subject, comprising a step of administering the composition according to claim 1 to the subject.

5. A method for suppressing the production of TSHR autoantibodies in a subject, comprising a step of administering the composition according to claim 2 to the subject.

6. A method for treating Graves' Disease in a subject comprising administering the composition according to claim 2 to the subject.

7. The method according to claim 3, wherein the subject is HLA-DR3.

8. The method according to claim 3, wherein the subject is HLA-DR4.

9. The method according to claim 3, in which the composition is administered following a dose-escalation protocol.

10. A kit which comprises the following peptides:
(i) a peptide comprising the amino acid sequence KKK-KYVSIDVTLQQLESHKKK (SEQ ID NO: 1), or a sequence having at least 85% sequence identity to SEQ ID NO:1; and
(ii) a peptide comprising the amino acid sequence GLK-MFPDLTKVYSTD (SEQ ID NO: 2), or a sequence having at least 85% sequence identity to SEQ ID NO: 2.

11. The kit of claim 10 further comprising an antithyroid agent and/or a β-blocker.

12. The composition of claim 1, further comprising at least one pharmaceutically acceptable excipient.

\* \* \* \* \*